(12) United States Patent
Mason

(10) Patent No.: US 11,515,021 B2
(45) Date of Patent: Nov. 29, 2022

(54) METHOD AND SYSTEM TO ANALYTICALLY OPTIMIZE TELEHEALTH PRACTICE-BASED BILLING PROCESSES AND REVENUE WHILE ENABLING REGULATORY COMPLIANCE

(71) Applicant: ROM TECHNOLOGIES, INC., Brookfield, CT (US)

(72) Inventor: Steven Mason, Las Vegas, NV (US)

(73) Assignee: Rom Technologies, Inc., Brookfield, CT (US)

( * ) Notice: Subject to any disclaimer, the term of this patent is extended or adjusted under 35 U.S.C. 154(b) by 108 days.

(21) Appl. No.: 16/987,087

(22) Filed: Aug. 6, 2020

(65) Prior Publication Data

US 2022/0044780 A1 Feb. 10, 2022

(51) Int. Cl.
*G16H 20/00* (2018.01)
*G06Q 20/10* (2012.01)
(Continued)

(52) U.S. Cl.
CPC ............ *G16H 20/00* (2018.01); *G06Q 20/102* (2013.01); *G06Q 40/02* (2013.01); *G16H 50/30* (2018.01); *G16H 80/00* (2018.01)

(58) Field of Classification Search
CPC ........ G16H 20/00; G16H 50/30; G16H 80/00; G06Q 20/102; G06Q 40/02
(Continued)

(56) References Cited

U.S. PATENT DOCUMENTS

| | | |
|---|---|---|
| 4,822,032 A | 4/1989 | Whitmore et al. |
| 4,932,650 A | 6/1990 | Bingham et al. |

(Continued)

FOREIGN PATENT DOCUMENTS

| | | |
|---|---|---|
| CA | 2698078 A1 | 3/2010 |
| CN | 112603295 A | 2/2003 |

(Continued)

OTHER PUBLICATIONS

Davenport et al., The Potential For Artificial Intelligence in Healthcare, 2019, Future Healthcare Journal 2019, vol. 6, No. 2: pp. 94-98, https://www.ncbi.nlm.nih.gov/pmc/articles/PMC6616181/pdf/futurehealth-6-2-94.pdf (Year: 2019).*

(Continued)

*Primary Examiner* — Joy Chng
(74) *Attorney, Agent, or Firm* — Dickinson Wright PLLC; Jonathan H. Harder; Stephen A. Mason

(57) ABSTRACT

A method for generating, by an artificial intelligence engine, a treatment plan and a billing sequence associated with the treatment plan is disclosed. The method includes receiving information pertaining to a patient. The information includes a medical diagnosis code of the patient. The method includes generating, based on the information, the treatment plan for the patient. The treatment plan includes instructions for the patient to follow. The method includes receiving a set of billing procedures associated with the instructions. The set of billing procedures includes rules pertaining to billing codes, timing, constraints, or some combination thereof. The method includes generating, based on the set of billing procedures, the billing sequence for at least a portion of the instructions. The billing sequence is tailored according to a certain parameter. The method includes transmitting the treatment plan and the billing sequence to a computing device.

20 Claims, 16 Drawing Sheets

(51) Int. Cl.
*G16H 80/00* (2018.01)
*G06Q 40/02* (2012.01)
*G16H 50/30* (2018.01)

(58) Field of Classification Search
USPC .................................................... 705/2–3
See application file for complete search history.

(56) References Cited

U.S. PATENT DOCUMENTS

| | | |
|---|---|---|
| 5,137,501 A | 8/1992 | Mertesdorf |
| 5,240,417 A | 8/1993 | Smithson et al. |
| 5,256,117 A | 10/1993 | Potts et al. |
| 5,284,131 A | 2/1994 | Gray |
| 5,429,140 A | 7/1995 | Burdea et al. |
| 5,738,636 A | 4/1998 | Saringer et al. |
| 6,110,130 A | 8/2000 | Kramer |
| 6,182,029 B1 | 1/2001 | Friedman |
| 6,267,735 B1 | 7/2001 | Blanchard et al. |
| 6,273,863 B1 | 8/2001 | Avni et al. |
| 6,413,190 B1 | 7/2002 | Wood et al. |
| 6,436,058 B1 | 8/2002 | Krahner et al. |
| 6,491,649 B1 | 12/2002 | Ombrellaro |
| 6,535,861 B1 | 3/2003 | OConnor et al. |
| 6,602,191 B2 | 8/2003 | Quy |
| 6,626,805 B1 | 9/2003 | Lightbody |
| 6,652,425 B1 | 11/2003 | Martin et al. |
| 6,890,312 B1 | 5/2005 | Priester et al. |
| 7,156,665 B1 | 1/2007 | OConnor et al. |
| 7,169,085 B1 | 1/2007 | Killin et al. |
| 7,209,886 B2 | 4/2007 | Kimmel |
| 7,226,394 B2 | 6/2007 | Johnson |
| RE39,904 E | 10/2007 | Lee |
| 7,507,188 B2 | 3/2009 | Nurre |
| 7,594,879 B2 | 9/2009 | Johnson |
| 7,778,851 B2 | 8/2010 | Schoenberg et al. |
| 7,809,601 B2 | 10/2010 | Shaya et al. |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,974,689 B2 | 7/2011 | Volpe et al. |
| 7,988,599 B2 | 8/2011 | Ainsworth et al. |
| 8,079,937 B2 | 12/2011 | Bedell et al. |
| 8,287,434 B2 | 10/2012 | Zavadsky et al. |
| 8,419,593 B2 | 4/2013 | Ainsworth et al. |
| 8,465,398 B2 | 6/2013 | Lee et al. |
| 8,506,458 B2 | 8/2013 | Dugan |
| 8,540,515 B2 | 9/2013 | Williams et al. |
| 8,540,516 B2 | 9/2013 | Williams et al. |
| 8,556,778 B1 | 10/2013 | Dugan |
| 8,613,689 B2 | 12/2013 | Dyer et al. |
| 8,672,812 B2 | 3/2014 | Dugan |
| 8,751,264 B2 | 6/2014 | Beraja et al. |
| 8,784,273 B2 | 7/2014 | Dugan |
| 8,823,448 B1 | 9/2014 | Shen |
| 8,979,711 B2 | 3/2015 | Dugan |
| 9,167,281 B2 | 10/2015 | Petrov et al. |
| 9,248,071 B1 | 2/2016 | Benda et al. |
| 9,272,185 B2 | 3/2016 | Dugan |
| 9,283,434 B1 | 3/2016 | Wu |
| 9,311,789 B1 | 4/2016 | Gwin |
| 9,367,668 B2 | 6/2016 | Flynt et al. |
| 9,409,054 B2 | 8/2016 | Dugan |
| 9,443,205 B2 | 9/2016 | Wall |
| 9,481,428 B2 | 11/2016 | Gros et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,717,947 B2 | 8/2017 | Lin |
| 9,737,761 B1 | 8/2017 | Govindarajan |
| 9,782,621 B2 | 10/2017 | Chiang et al. |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 10,074,148 B2 | 9/2018 | Cashman et al. |
| 10,130,298 B2 | 11/2018 | Mokaya et al. |
| 10,155,134 B2 | 12/2018 | Dugan |
| 10,159,872 B2 | 12/2018 | Sasaki et al. |
| 10,173,094 B2 | 1/2019 | Gomberg et al. |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,226,663 B2 | 3/2019 | Gomberg et al. |
| 10,325,070 B2 | 6/2019 | Beale et al. |
| 10,327,697 B1 | 6/2019 | Stein et al. |
| 10,424,033 B2 | 9/2019 | Romeo |
| 10,430,552 B2 | 10/2019 | Mihai |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| 10,792,495 B2 | 10/2020 | Izvorski et al. |
| 10,874,905 B2 | 12/2020 | Belson et al. |
| D907,143 S | 1/2021 | Ach et al. |
| 10,918,332 B2 | 2/2021 | Belson et al. |
| 10,931,643 B1 | 2/2021 | Neumann |
| 11,000,735 B2 | 5/2021 | Orady et al. |
| 11,045,709 B2 | 6/2021 | Putnam |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Am et al. |
| D939,644 S | 12/2021 | Ach et al. |
| D940,797 S | 1/2022 | Ach et al. |
| 11,229,727 B2 | 1/2022 | Tatonetti |
| 11,270,795 B2 | 3/2022 | Mason et al. |
| 11,272,879 B2 | 3/2022 | Wiedenhoefer et al. |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 11,404,150 B2 | 8/2022 | Guaneri et al. |
| 11,410,768 B2 | 8/2022 | Mason et al. |
| 2002/0072452 A1 | 6/2002 | Torkelson |
| 2002/0160883 A1 | 10/2002 | Dugan |
| 2003/0036683 A1 | 2/2003 | Kehr et al. |
| 2003/0064863 A1 | 4/2003 | Chen |
| 2003/0181832 A1 | 9/2003 | Carnahan et al. |
| 2004/0102931 A1 | 5/2004 | Ellis et al. |
| 2004/0147969 A1 | 7/2004 | Mann et al. |
| 2005/0043153 A1 | 2/2005 | Krietzman |
| 2006/0064329 A1 | 3/2006 | Abolfathi et al. |
| 2007/0042868 A1 | 2/2007 | Fisher et al. |
| 2007/0137307 A1 | 6/2007 | Gruben et al. |
| 2007/0173392 A1 | 7/2007 | Stanford |
| 2007/0287597 A1 | 12/2007 | Cameron |
| 2008/0021834 A1 | 1/2008 | Holla et al. |
| 2008/0153592 A1 | 6/2008 | James-Herbert |
| 2008/0300914 A1 | 12/2008 | Karkanias et al. |
| 2009/0011907 A1 | 1/2009 | Radow et al. |
| 2009/0058635 A1 | 3/2009 | LaLonde et al. |

(56) References Cited

U.S. PATENT DOCUMENTS

| | | |
|---|---|---|
| 2009/0070138 A1 | 3/2009 | Langheier et al. |
| 2009/0270227 A1 | 10/2009 | Ashby et al. |
| 2010/0048358 A1 | 2/2010 | Tchao et al. |
| 2010/0121160 A1 | 5/2010 | Stark et al. |
| 2010/0173747 A1 | 7/2010 | Chen et al. |
| 2010/0248899 A1 | 9/2010 | Bedell et al. |
| 2010/0268304 A1 | 10/2010 | Matos |
| 2010/0298102 A1 | 11/2010 | Bosecker et al. |
| 2011/0047108 A1 | 2/2011 | Chakrabarty et al. |
| 2011/0172059 A1 | 7/2011 | Watterson et al. |
| 2011/0218814 A1 | 9/2011 | Coats |
| 2011/0275483 A1 | 11/2011 | Dugan |
| 2012/0065987 A1 | 3/2012 | Farooq et al. |
| 2012/0116258 A1 | 5/2012 | Lee |
| 2012/0183939 A1 | 7/2012 | Aragones et al. |
| 2012/0190502 A1 | 7/2012 | Paulus et al. |
| 2012/0295240 A1 | 11/2012 | Walker et al. |
| 2012/0310667 A1 | 12/2012 | Altman et al. |
| 2013/0123667 A1 | 5/2013 | Komatireddy et al. |
| 2013/0137550 A1 | 5/2013 | Skinner et al. |
| 2013/0178334 A1 | 7/2013 | Brammer |
| 2013/0296987 A1 | 11/2013 | Rogers et al. |
| 2013/0318027 A1 | 11/2013 | Almogy et al. |
| 2014/0006042 A1 | 1/2014 | Keefe et al. |
| 2014/0011640 A1 | 1/2014 | Dugan |
| 2014/0113768 A1 | 4/2014 | Lin et al. |
| 2014/0155129 A1 | 6/2014 | Dugan |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0309083 A1 | 10/2014 | Dugan |
| 2014/0322686 A1 | 10/2014 | Kang |
| 2015/0045700 A1 | 2/2015 | Cavanagh et al. |
| 2015/0088544 A1 | 3/2015 | Goldberg |
| 2015/0151162 A1 | 6/2015 | Dugan |
| 2015/0158549 A1 | 6/2015 | Gros et al. |
| 2015/0161331 A1 | 6/2015 | Oleynik |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0379232 A1 | 12/2015 | Mainwaring et al. |
| 2016/0007885 A1 | 1/2016 | Basta et al. |
| 2016/0117471 A1 | 4/2016 | Belt et al. |
| 2016/0140319 A1 | 5/2016 | Stark et al. |
| 2016/0151670 A1 | 6/2016 | Dugan |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2017/0004260 A1* | 1/2017 | Moturu ............... G16H 10/60 |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0095670 A1 | 4/2017 | Ghaffar et al. |
| 2017/0095692 A1 | 4/2017 | Chang et al. |
| 2017/0095693 A1 | 4/2017 | Chang et al. |
| 2017/0106242 A1 | 4/2017 | Dugan |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147789 A1 | 5/2017 | Wiedenhoefer et al. |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0209766 A1 | 7/2017 | Riley et al. |
| 2017/0243028 A1 | 8/2017 | LaFever et al. |
| 2017/0266501 A1 | 9/2017 | Sanders et al. |
| 2017/0278209 A1 | 9/2017 | Olsen et al. |
| 2017/0282015 A1 | 10/2017 | Wicks et al. |
| 2017/0300654 A1* | 10/2017 | Stein ..................... H01Q 1/42 |
| 2017/0312614 A1 | 11/2017 | Tran et al. |
| 2017/0329917 A1* | 11/2017 | McRaith ............ G16H 40/67 |
| 2017/0333755 A1 | 11/2017 | Rider |
| 2017/0337033 A1 | 11/2017 | Duyan et al. |
| 2017/0337334 A1* | 11/2017 | Stanczak ............ G06Q 30/04 |
| 2017/0344726 A1 | 11/2017 | Duffy et al. |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0052962 A1 | 2/2018 | Van Der Koijk et al. |
| 2018/0056104 A1 | 3/2018 | Cromie et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0102190 A1 | 4/2018 | Hogue et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0240552 A1* | 8/2018 | Tuyl .................... G16H 50/20 |
| 2018/0253991 A1 | 9/2018 | Tang et al. |
| 2018/0256079 A1 | 9/2018 | Yang et al. |
| 2018/0263530 A1 | 9/2018 | Jung |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296157 A1 | 10/2018 | Bleich et al. |
| 2018/0330058 A1 | 11/2018 | Bates |
| 2018/0330824 A1 | 11/2018 | Athey et al. |
| 2018/0360340 A1 | 12/2018 | Rehse et al. |
| 2018/0373844 A1* | 12/2018 | Ferrandez-Escamez ................... G16H 50/20 |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0088356 A1 | 3/2019 | Oliver et al. |
| 2019/0111299 A1 | 4/2019 | Radcliffe et al. |
| 2019/0115097 A1 | 4/2019 | Macoviak et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Celia et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0200920 A1 | 7/2019 | Tien et al. |
| 2019/0209891 A1 | 7/2019 | Fung |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0269343 A1 | 9/2019 | Ramos Murguialday et al. |
| 2019/0274523 A1 | 9/2019 | Bates et al. |
| 2019/0304584 A1 | 10/2019 | Savolainen |
| 2019/0366146 A1 | 12/2019 | Tong et al. |
| 2019/0388728 A1 | 12/2019 | Wang et al. |
| 2020/0066390 A1 | 2/2020 | Svendrys et al. |
| 2020/0085300 A1 | 3/2020 | Kwatra et al. |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1* | 5/2020 | Pulitzer ............... G16H 50/70 |
| 2020/0160198 A1 | 5/2020 | Reeves et al. |
| 2020/0170876 A1 | 6/2020 | Kapure et al. |
| 2020/0176098 A1 | 6/2020 | Lucas et al. |

(56) References Cited

U.S. PATENT DOCUMENTS

| | | |
|---|---|---|
| 2020/0197744 A1 | 6/2020 | Schweighofer |
| 2020/0221975 A1 | 7/2020 | Basta et al. |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0334972 A1 | 10/2020 | Gopalakrishnan |
| 2020/0357299 A1 | 11/2020 | Patel et al. |
| 2020/0395112 A1 | 12/2020 | Ronner |
| 2020/0401224 A1 | 12/2020 | Cotton |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0202090 A1 | 7/2021 | ODonovan et al. |
| 2021/0202103 A1 | 7/2021 | Bostic et al. |
| 2021/0244998 A1 | 8/2021 | Hacking et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0407670 A1 | 12/2021 | Mason et al. |
| 2021/0407681 A1 | 12/2021 | Mason et al. |
| 2022/0015838 A1 | 1/2022 | Posnack et al. |
| 2022/0047921 A1 | 2/2022 | Bissonnette et al. |
| 2022/0079690 A1 | 3/2022 | Mason et al. |
| 2022/0080256 A1 | 3/2022 | Arn et al. |
| 2022/0105384 A1 | 4/2022 | Hacking et al. |
| 2022/0105385 A1 | 4/2022 | Hacking et al. |
| 2022/0115133 A1 | 4/2022 | Mason et al. |
| 2022/0126169 A1 | 4/2022 | Mason |
| 2022/0148725 A1 | 5/2022 | Mason et al. |
| 2022/0158916 A1 | 5/2022 | Mason et al. |
| 2022/0193491 A1 | 6/2022 | Mason et al. |
| 2022/0230729 A1 | 7/2022 | Mason et al. |
| 2022/0238223 A1 | 7/2022 | Mason et al. |
| 2022/0262483 A1 | 8/2022 | Rosenberg et al. |
| 2022/0266094 A1 | 8/2022 | Mason et al. |
| 2022/0270738 A1 | 8/2022 | Mason et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |

FOREIGN PATENT DOCUMENTS

| | | |
|---|---|---|
| CN | 103488880 A | 1/2014 |
| CN | 104335211 A | 2/2015 |
| CN | 105683977 A | 6/2016 |
| CN | 105894088 A | 8/2016 |
| CN | 105930668 A | 9/2016 |
| CN | 106127646 A | 11/2016 |
| CN | 106510985 A | 3/2017 |
| CN | 107066819 A | 8/2017 |
| CN | 107430641 A | 12/2017 |
| CN | 107736982 A | 2/2018 |
| CN | 108078737 A | 5/2018 |
| CN | 208573971 U | 3/2019 |
| CN | 110148472 A | 8/2019 |
| CN | 110215188 A | 9/2019 |
| CN | 111105859 A | 5/2020 |
| CN | 111370088 A | 7/2020 |
| CN | 112603295 A | 4/2021 |
| DE | 102018202497 A1 | 8/2018 |
| DE | 102018211212 A1 | 1/2019 |
| DE | 102019108425 B3 | 8/2020 |
| EP | 3323473 A1 | 5/2018 |
| EP | 3688537 A1 | 8/2020 |
| EP | 3731733 A1 | 11/2020 |
| JP | 2003225875 A | 8/2003 |
| JP | 2013515995 A | 5/2013 |
| JP | 3198173 U | 6/2015 |
| JP | 2019134909 A | 8/2019 |
| JP | 6573739 B1 | 9/2019 |
| JP | 6659831 B2 | 3/2020 |
| JP | 6710357 B1 | 6/2020 |
| JP | 6775757 B1 | 10/2020 |
| JP | 2021027917 A | 2/2021 |
| KR | 20020009724 A | 2/2002 |
| KR | 20020065253 A | 8/2002 |
| KR | 20150017693 A | 2/2015 |
| KR | 20160093990 A | 8/2016 |
| KR | 20170038837 A | 4/2017 |
| KR | 101988167 B1 | 6/2019 |
| KR | 20200025290 A | 3/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102142713 B1 | 8/2020 |
| KR | 102162522 B1 | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102264498 B1 | 6/2021 |
| WO | 0149235 A2 | 7/2001 |
| WO | 0151083 A2 | 7/2001 |
| WO | 2001050387 A1 | 7/2001 |
| WO | 2003043494 | 5/2003 |
| WO | 2006004430 A2 | 1/2006 |
| WO | 2008114291 A1 | 9/2008 |
| WO | 2016154318 A1 | 9/2016 |
| WO | 2018171853 A1 | 9/2018 |
| WO | 2019022706 A1 | 1/2019 |
| WO | 2019204876 A1 | 4/2019 |
| WO | 2020185769 A1 | 3/2020 |
| WO | 2020075190 A1 | 4/2020 |
| WO | 2020130979 A1 | 6/2020 |
| WO | 2020149815 A2 | 7/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |

(56) References Cited

FOREIGN PATENT DOCUMENTS

| WO | 2021038980 A1 | 3/2021 |
| WO | 2021055427 A1 | 3/2021 |
| WO | 2021055491 A1 | 3/2021 |
| WO | 2021061061 A1 | 4/2021 |
| WO | 2021081094 A1 | 4/2021 |
| WO | 2021138620 A1 | 7/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |

OTHER PUBLICATIONS

Davenport et al.: The Potential for Artificial Intelligences in Healthcare, 2019, Future Healthcare Journal 2019, vol. 6, No. 2: pp. 94-98, https://www.ncbi.nlm.gov/pmc/articles/PMC661681/pdf/futurehealth-6-2- 94.pdf (Year: 2019).*

Ahmed et al., Artificial Intelligence With Multi-Functional Machine Learning Platform Development for Better Healthcare and Precision Medicine, 2020, Database (Oxford), 2020:baaa010. Doi:10.1093/database/baaa010 (Year: 2020).*

International Searching Authority, Search Report and Written Opinion for International Application No. PCT/US2021/032807, dated Sep. 6, 2021, 11 pages.

Jennifer Bresnick, "What is the Role of Natural Language Processing in Healthcare?", pp. 1-7, published Aug. 18, 2016, retrieved on Feb. 1, 2022 from https://healthitanalytics.com/featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Davenport et al., "The Potential for Artificial Intelligence in Healthcare", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

Lima de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities for Artificial Intelligence to Transform How Care is Delivered," Nov. 2019, American Hospital Association, pp. 1-12.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.

Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.

Kuiken et al., "Computerized Biofeedback Knee Goniometer: Acceptance and Effect on Exercise Behavior in Posttotal Knee Arthroplasty Rehabilitation," Biomedical Engineering Faculty Research and Publications, 2004, pp. 1-10.

Ahmed et al., "Artificial intelligence with multi-functional machine learning platform development for better healthcare and precision medicine," Database, 2020, pp. 1-35.

Davenport et al., "The potential for artificial intelligence in healthcare," Digital Technology, Future Healthcare Journal, 2019, pp. 1-5, vol. 6, No. 2.

Website for "OxeFitXS1", pp. 1-3, retrieved on Sep. 9, 2022 from https://www.oxefit.com/xs1.

Website for "Preva Mobile", pp. 1-6, retrieved on Sep. 9, 2022 from https://www.precor.com/en-us/resources/introducing-preva-mobile.

Website for "J-Bike", pp. 1-3, retrieved on Sep. 9, 2022 from https://www.magneticdays.com/en/cycling-for-physical-rehabilitation.

Website for "Excy", pp. 1-12, retrieved on Sep. 9, 2022 from https://excy.com/portable-exercise-rehabilitation-excy-xcs-pro/.

Website for "OxeFitXP1", p. 1, retrieved on Sep. 9, 2022 from https://www.oxefit.com/xp1.

* cited by examiner

METHOD AND SYSTEM TO ANALYTICALLY OPTIMIZE TELEHEALTH PRACTICE-BASED BILLING PROCESSES AND REVENUE WHILE ENABLING REGULATORY COMPLIANCE

BACKGROUND

Remote medical assistance, or telemedicine, may aid a patient in performing various aspects of a rehabilitation regimen for a body part. The patient may use a patient interface in communication with an assistant interface for receiving the remote medical assistance via audio and/or audiovisual communications.

SUMMARY

In one embodiment, a method for generating, by an artificial intelligence engine, a treatment plan and a billing sequence associated with the treatment plan is disclosed. The method includes receiving information pertaining to a patient. The information includes a medical diagnosis code of the patient. The method includes generating, based on the information, the treatment plan for the patient. The treatment plan includes instructions for the patient to follow. The method includes receiving a set of billing procedures associated with the instructions. The set of billing procedures includes rules pertaining to billing codes, timing, constraints, or some combination thereof. The method includes generating, based on the set of billing procedures, the billing sequence for at least a portion of the instructions. The billing sequence is tailored according to a certain parameter. The method includes transmitting the treatment plan and the billing sequence to a computing device.

In one embodiment, a system includes a memory that stores instructions and a processing device communicatively coupled to the memory. The processing device executes the instructions to perform any of the methods, operations, or steps described herein.

In one embodiment, a tangible, non-transitory computer-readable medium stores instructions that, when executed, cause a processing device to perform any of the methods, operations, or steps described herein.

BRIEF DESCRIPTION OF THE DRAWINGS

For a detailed description of example embodiments, reference will now be made to the accompanying drawings in which.

NOTATION AND NOMENCLATURE

Figure 1:
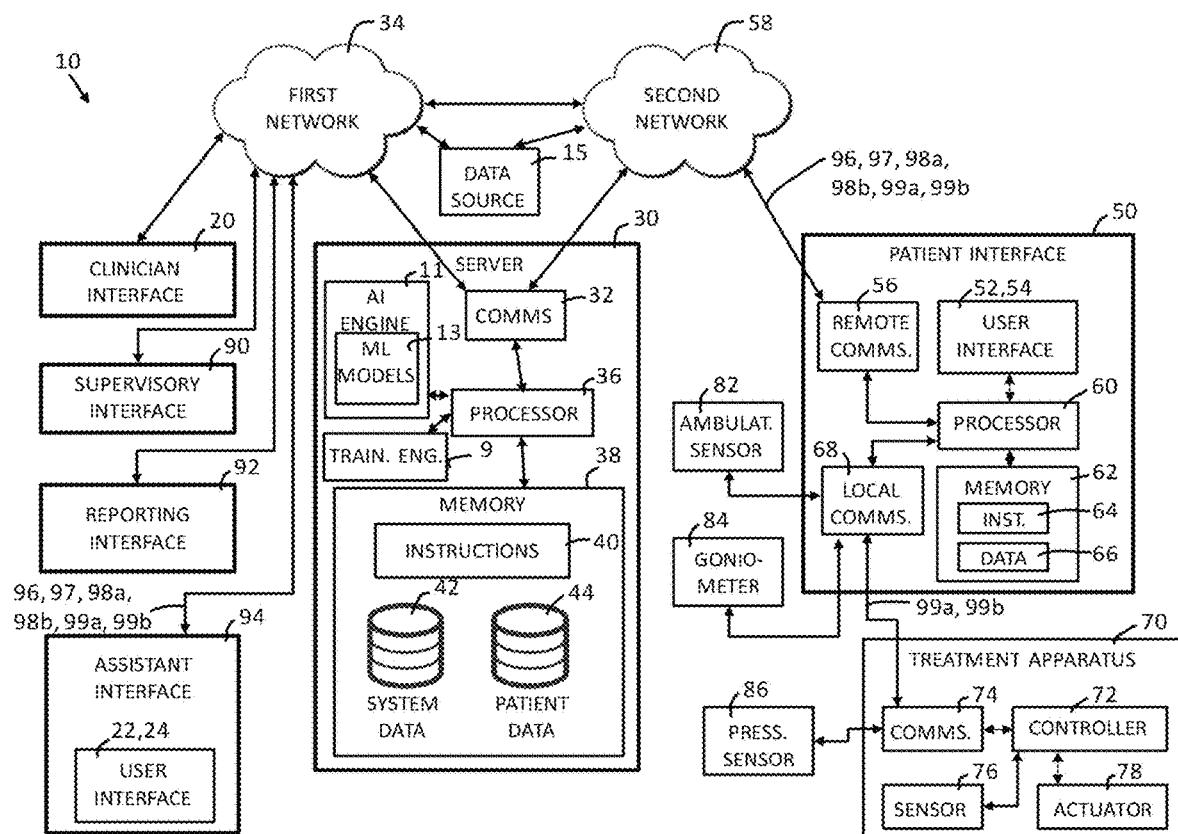
FIG. 1 shows a block diagram of an embodiment of a computer implemented system for managing a treatment plan according to the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The terms telemedicine, telehealth, telemed, teletherapeutic, etc. may be used interchangeably herein.

The term "monetary value amount" (singular or plural) may refer to fees, revenue, profit (e.g., gross, net, etc.), earnings before interest (EBIT), earnings before interest, depreciation and amortization (EBITDA), cash flow, free cash flow, working capital, gross revenue, a value of warrants, options, equity, debt, derivatives or any other financial instrument, any generally acceptable financial measure or metric in corporate finance or according to Generally Accepted Accounting Principles (GAAP) or foreign counterparts, or the like.

The term "optimal treatment plan" may refer to optimizing a treatment plan based on a certain parameter or combinations of more than one parameter, such as, but not limited to, a monetary value amount generated by a treatment plan and/or billing sequence, wherein the monetary value amount is measured by an absolute amount in dollars or another currency, a Net Present Value (NPV) or any other measure, a patient outcome that results from the treatment plan and/or billing sequence, a fee paid to a medical professional, a payment plan for the patient to pay off an amount of money owed or a portion thereof, a plan of reimbursement, an amount of revenue, profit or other monetary value amount to be paid to an insurance or third-party provider, or some combination thereof.

The term billing sequence may refer to an order in which billing codes associated with procedures or instructions of a treatment plan are billed.

The term billing codes may refer any suitable type of medical coding, such as Current Procedural Terminology (CPT), Diagnosis Related Groups (DRGs), International Classification of Disease, Tenth Edition (ICD-10), and Healthcare Common Procedural Coding System (HCPCS).

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining a treatment plan for a patient having certain characteristics (e.g., vital-sign or other measurements; performance; demographic; geographic; diagnostic; measurement- or test-based; medically historic; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, or some combination thereof. The measurement information may include, e.g., a vital sign, a respiration rate, a heartrate, a temperature, a blood pressure, or some combination thereof. It may be desirable to process the characteristics of a multitude of patients, the treatment plans performed for those patients, and the results of the treatment plans for those patients.

Further, another technical problem may involve distally treating, via a computing device during a telemedicine or telehealth session, a patient from a location different than a location at which the patient is located. An additional technical problem is controlling or enabling the control of, from the different location, a treatment apparatus used by the patient at the location at which the patient is located. Oftentimes, when a patient undergoes rehabilitative surgery (e.g., knee surgery), a physical therapist or other medical professional may prescribe a treatment apparatus to the patient to use to perform a treatment protocol at their residence or any mobile location or temporary domicile. A medical professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

Since the physical therapist or other medical professional is located in a different location from the patient and the treatment apparatus, it may be technically challenging for the physical therapist or other medical professional to monitor the patient's actual progress (as opposed to relying on the patient's word about their progress) using the treatment apparatus, modify the treatment plan according to the patient's progress, adapt the treatment apparatus to the personal characteristics of the patient as the patient performs the treatment plan, and the like.

Accordingly, some embodiments of the present disclosure pertain to using artificial intelligence and/or machine learning to assign patients to cohorts and to dynamically control a treatment apparatus based on the assignment during an adaptive telemedical session. In some embodiments, numerous treatment apparatuses may be provided to patients. The treatment apparatuses may be used by the patients to perform treatment plans in their residences, at a gym, at a rehabilitative center, at a hospital, or any suitable location, including permanent or temporary domiciles. In some embodiments, the treatment apparatuses may be communicatively coupled to a server. Characteristics of the patients may be collected before, during, and/or after the patients perform the treatment plans. For example, the personal information, the performance information, and the measurement information may be collected before, during, and/or after the person performs the treatment plans. The results (e.g., improved performance or decreased performance) of performing each exercise may be collected from the treatment apparatus throughout the treatment plan and after the treatment plan is performed. The parameters, settings, configurations, etc. (e.g., position of pedal, amount of resistance, etc.) of the treatment apparatus may be collected before, during, and/or after the treatment plan is performed.

Each characteristic of the patient, each result, and each parameter, setting, configuration, etc. may be timestamped and may be correlated with a particular step in the treatment plan. Such a technique may enable determining which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment apparatuses and/or any suitable computing device (e.g., computing devices where personal information is entered, such as a clinician interface or patient interface) over time as the patients use the treatment apparatuses to perform the various treatment plans. The data that may be collected may include the characteristics of the patients, the treatment plans performed by the patients, and the results of the treatment plans.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment apparatus for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment apparatus while the new patient uses the treatment apparatus to perform the treatment plan.

As may be appreciated, the characteristics of the new patient may change as the new patient uses the treatment apparatus to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion. A different treatment plan may be selected for the new patient, and the treatment apparatus may be controlled, distally and based on the different treatment plan, the treatment apparatus while the new patient uses the treatment apparatus to perform the treatment plan. Such techniques may provide the technical solution of distally controlling a treatment apparatus. Further, the techniques may lead to faster recovery times and/or better results for the patients because the treatment plan that most accurately fits their characteristics is selected and implemented, in real-time, at any given moment. Real-time may refer to less than or equal to 2 seconds. Near real-time may refer to any interaction of a sufficiently short time to enable two individuals to engage in a dialogue via such user interface, and will generally be less than 10 seconds but greater than 2 seconds. As described herein, the term "results" may refer to medical results or medical outcomes. Results and outcomes may refer to responses to medical actions.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may also be trained to output treatment plans that are not optimal or sub-optimal or even inappropriate (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient.

In some embodiments, the treatment plans and/or excluded treatment plans may be presented, during a telemedicine or telehealth session, to a medical professional. The medical professional may select a particular treatment plan for the patient to cause that treatment plan to be transmitted to the patient and/or to control, based on the treatment plan, the treatment apparatus. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment apparatus. In such cases, the recommended treatment plans and/or excluded treatment plans may be presented simultaneously with a video of the patient in real-time or near real-time during a telemedicine or telehealth session on a user interface of a computing device of a medical professional. The video may also be accompanied by audio, text and other multimedia information. Real-time may refer to less than or equal to 2 seconds. Near real-time may refer to any interaction of a sufficiently short time to enable two individuals to engage in a dialogue via such user interface, and will generally be less than 10 seconds but greater than 2 seconds.

Presenting the treatment plans generated by the artificial intelligence engine concurrently with a presentation of the patient video may provide an enhanced user interface because the medical professional may continue to visually and/or otherwise communicate with the patient while also reviewing the treatment plans on the same user interface. The enhanced user interface may improve the medical professional's experience using the computing device and may encourage the medical professional to reuse the user interface. Such a technique may also reduce computing resources (e.g., processing, memory, network) because the medical professional does not have to switch to another user interface screen to enter a query for a treatment plan to recommend based on the characteristics of the patient. The artificial intelligence engine provides, dynamically on the fly, the treatment plans and excluded treatment plans.

Additionally, some embodiments of the present disclosure may relate to analytically optimizing telehealth practice-based billing processes and revenue while enabling regulatory compliance. Information of a patient's condition may be received and the information may be used to determine the procedures (e.g., the procedures may include one or more office visits, bloodwork tests, other medical tests, surgeries, biopsies, performances of exercise or exercises, therapy sessions, physical therapy sessions, lab studies, consultations, or the like) to perform on the patient. Based on the information, a treatment plan may be generated for the patient. The treatment plan may include various instructions pertaining at least to the procedures to perform for the patient's condition. There may be an optimal way to bill the procedures and costs associated with the billing. However, there may be a set of billing procedures associated with the set of instructions. The set of billing procedures may include a set of rules pertaining to billing codes, timing, constraints, or some combination thereof that govern the order in which the procedures are allowed to be billed and, further, which procedures are allowed to be billed or which portions of a given procedure are allowed to be billed. For example, regarding timing, a test may be allowed to be conducted before surgery but not after the surgery. In his example, it may be best for the patient to conduct the test before the surgery. Accordingly, the billing sequence may include a billing code for the test before a billing code for the surgery. The constraints may pertain to an insurance regime, a medical order, laws, regulations, or the like. Regarding the order, an example may include: if procedure A is performed, then procedure B may be billed, but procedure A cannot be billed if procedure B was billed first. It may not be a trivial task to optimize a billing sequence for a treatment plan while complying with the set of rules.

It is desirable to generate a billing sequence for the patient's treatment plan that complies with the set of rules. In addition, there are multiples of parameters to consider for a desired billing sequence. The parameters may pertain to a monetary value amount generated by the billing sequence, a patient outcome that results from the treatment plan associated with the billing sequence, a fee paid to a medical professional, a payment plan for the patient to pay off an amount of money owed, a plan of reimbursement, an amount of revenue to be paid to an insurance provider, or some combination thereof.

The artificial intelligence engine may be trained to generate, based on the set of billing procedures, one or more billing sequences for at least a portion of or all of the instructions, where the billing sequence is tailored according to one or more of the parameters. As such, the disclosed techniques may enable medical professionals to provide, improve or come closer to achieving best practices for ethical patient care. By complying with the set of billing procedures, the disclosed techniques provide for ethical consideration of the patient's care, while also benefiting the practice of the medical professional and benefiting the interests of insurance providers. In other words, one key goal of the disclosed techniques is to maximize both patient care quality and the degree of reimbursement for the use of ethical medical practices related thereto.

The artificial intelligence engine may pattern match to generate billing sequences and/or treatment plans tailored for a selected parameter (e.g., best outcome for the patient, maximize monetary value amount generated, etc.). Different machine learning models may be trained to generate billing sequences and/or treatment plans for different parameters. In some embodiments, one trained machine learning model that generates a first billing sequence for a first parameter (e.g., monetary value amount generated) may be linked to and feed its output to another trained machine learning model that generates a second billing sequence for a second parameter (e.g., a plan of reimbursement). Thus, the second billing sequence may be tuned for both the first parameter and the second parameter. It should be understood that any suitable combination of trained machine learning models may be used to provide billing sequences and/or treatment plans tailored to any combination of the parameters described herein, as well as other parameters contemplated and/or used in billing sequences and/or treatment plans, whether or not specifically expressed or enumerated herein.

In some embodiments, a medical professional and an insurance company may participate to provide requests pertaining to the billing sequence. For example, the medical professional and the insurance company may request to receive immediate reimbursement for the treatment plan. Accordingly, the artificial intelligence engine may be trained to generate, based on the immediate reimbursement requests, a modified billing sequence that complies with the set of billing procedures and provides for immediate reimbursement to the medical professional and the insurance company.

In some embodiments, the treatment plan may be modified by a medical professional. For example, certain procedures may be added, modified or removed. In the telehealth scenario, there are certain procedures that may not be performed due to the distal nature of a medical professional using a computing device in a different physical location than a patient.

In some embodiments, the treatment plan and the billing sequence may be transmitted to a computing device of a medical professional, insurance provider, any lawfully designated or appointed entity and/or patient. It should be noted that there may be other entities that receive the treatment plan and the billing sequence for the insurance provider and/or the patient. Such entities may include any lawfully designated or appointed entity (e.g., assignees, legally predicated designees, attorneys-in-fact, legal proxies, etc.), Thus, as used herein, it should be understood that these entities may receive information in lieu of, in addition to the insurance provider and/or the patient, or as an intermediary or interlocutor between another such lawfully designated or appointed entity and the insurance provider and/or the patient. The treatment plan and the billing sequence may be presented in a first portion of a user interface on the computing device. A video of the patient or the medical professional may be optionally presented in a second portion of the user interface on the computing device. The first portion (including the treatment plan and the billing sequence) and the second portion (including the video) may be presented concurrently on the user interface to enable to the medical professional and/or the patient to view the video and the treatment plan and the billing sequence at the same time. Such a technique may be beneficial and reduce computing resources because the user (medical professional and/or patient) does not have to minimize the user interface (including the video) in order to open another user interface which includes the treatment plan and the billing sequence.

In some embodiments, the medical professional and/or the patient may select a certain treatment plan and/or billing sequence from the user interface. Based on the selection, the treatment apparatus may be electronically controlled, either via the computing device of the patient transmitting a control signal to a controller of the treatment apparatus, or via the computing device of the medical professional transmitting a control signal to the controller of the treatment apparatus. As such, the treatment apparatus may initialize the treatment plan and configure various settings (e.g., position of pedals, speed of pedaling, amount of force required on pedals, etc.) defined by the treatment plan.

A potential technical problem may relate to the information pertaining to the patient's medical condition being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). That is, some sources used by various medical professional entities may be installed on their local computing devices and, additionally and/or alternatively, may use proprietary formats. Accordingly, some embodiments of the present disclosure may use an API to obtain, via interfaces exposed by APIs used by the sources, the formats used by the sources. In some embodiments, when information is received from the sources, the API may map and convert the format used by the sources to a standardized (i.e., canonical) format, language and/or encoding ("format" as used herein will be inclusive of all of these terms) used by the artificial intelligence engine. Further, the information converted to the standardized format used by the artificial intelligence engine may be stored in a database accessed by the artificial intelligence engine when the artificial intelligence engine is performing any of the techniques disclosed herein. Using the information converted to a standardized format may enable a more accurate determination of the procedures to perform for the patient and/or a billing sequence to use for the patient.

To that end, the standardized information may enable generating treatment plans and/or billing sequences having a particular format that can be processed by various applications (e.g., telehealth). For example, applications, such as telehealth applications, may be executing on various computing devices of medical professionals and/or patients. The applications (e.g., standalone or web-based) may be provided by a server and may be configured to process data according to a format in which the treatment plans and the billing sequences are implemented. Accordingly, the disclosed embodiments may provide a technical solution by (i) receiving, from various sources (e.g., EMR systems), information in non-standardized and/or different formats; (ii) standardizing the information (i.e., representing the information in a canonical format); and (iii) generating, based on the standardized information, treatment plans and billing sequences having standardized formats capable of being processed by applications (e.g., telehealth applications) executing on computing devices of medical professionals and/or patients and/or their lawfully authorized designees.

Additionally, some embodiments of the present disclosure may use artificial intelligence and machine learning to create optimal patient treatment plans based on one or more of monetary value amount and patient outcomes. Optimizing for one or more of patient outcome and monetary value amount generated, while complying with a set of constraints, may be a computationally and technically challenging issue.

Accordingly, the disclosed techniques provide numerous technical solutions in embodiments that enable dynamically determining one or more optimal treatment plans optimized for various parameters (e.g., monetary value amount generated, patient outcome, risk, etc.). In some embodiments, while complying with the set of constraints, an artificial intelligence engine may use one or more trained machine learning models to generate the optimal treatment plans for various parameters. The set of constraints may pertain to billing codes associated with various treatment plans, laws, regulations, timings of billing, orders of billing, and the like. As described herein, one or more of the optimal treatment plans may be selected to control, based on the selected one or more treatment plans, the treatment apparatus in real-time or near real-time while a patient uses the treatment apparatus in a telehealth or telemedicine session.

One of the parameters may include maximizing an amount of monetary value amount generated. Accordingly, in one embodiment, the artificial intelligence engine may receive information pertaining to a medical condition of the patient. Based on the information, the artificial intelligence engine may receive a set of treatment plans that, when applied to other patients having similar medical condition information, cause outcomes to be achieved by the patients. The artificial intelligence engine may receive a set of monetary value amounts associated with the set of treatment plans. A respective monetary value amount may be associated with a respective treatment plan. The artificial intelligence engine may receive the set of constraints. The artificial intelligence engine may generate optimal treatment plans for a patient, where the generating is based on one or more of the set of treatment plans, the set of monetary value amounts, and the set of constraints. Each of the optimal treatment plans complies completely or to the maximum extent possible or to a prescribed extent with the set of constraints and represents a patient outcome and an associated monetary value amount generated. The optimal treatment plans may be transmitted, in real-time or near real-time, during a telehealth or telemedicine session, to be presented on one or more computing devices of one or more medical professionals and/or one or more patients. It should be noted that the term "telehealth" as used herein will be inclusive of all of the following terms: telemedicine, teletherapeutic, telerehab, etc. It should be noted that the term "telemedicine" as used herein will be inclusive of all of the following terms: telehealth, teletherapeutic, telerehab, etc.

A user may select different monetary value amounts, and the artificial intelligence engine may generate different optimal treatment plans for those monetary value amounts. The different optimal treatment plans may represent different patient outcomes and may also comply with the set of constraints. The different optimal treatment plans may be transmitted, in real-time or near real-time, during a telehealth or telemedicine session, to be presented on a computing device of a medical professional and/or a patient.

The disclosed techniques may use one or more equations having certain parameters on a left side of the equation and certain parameters on a right side of the equation. For example, the parameters on the left side of the equation may represent a treatment plan, patient outcome, risk, and/or monetary value amount generated. The parameters on the right side of the equation may represent the set of constraints that must be complied with to ethically and/or legally bill for the treatment plan. Such an equation or equations and/or one or more parameters therein may also, without limitation, incorporate or implement appropriate mathematical, statistical and/or probabilistic algorithms as well as use computer-based subroutines, methods, operations, function calls, scripts, services, applications or programs to receive certain values and to return other values and/or results. The various parameters may be considered levers that may be adjusted to provide a desired treatment plan and/or monetary value amount generated. In some instances, it may be desirable to select an optimal treatment plan that is tailored for a desired patient outcome (e.g., best recovery, fastest recovery rate, etc.), which may effect the monetary value amount generated and the risk associated with the treatment plan. In other instances, it may be desirable to select an optimal treatment plan tailored for a desired monetary value amount generated, which may effect the treatment plan and/or the risk associated with the treatment plan.

For example, a first treatment plan may result in a first patient outcome having a low risk and resulting in a low monetary value amount generated, whereas a second treatment plan may result in a second patient outcome (better than the first patient outcome) having a higher risk and resulting in a higher monetary value amount generated than the first treatment plan. Both the first treatment plan and the second treatment plan are generated based on the set of constraints. Also, both the first treatment plan and the second treatment plan may be simultaneously presented, in real-time or near real-time, on a user interface of one or more computing devices engaged in a telehealth or telemedicine session. A user (e.g., medical professional or patient) may select either the first or second treatment plan to cause the selected treatment plan to be implemented on the treatment apparatus. In other words, the treatment apparatus may be electronically controlled based on the selected treatment plan.

Accordingly, the artificial intelligence engine may use various machine learning models, each trained to generate one or more optimal treatment plans for a different parameter, as described further below. Each of the one or more optimal treatment plans complies with the set of constraints.

The various embodiments disclosed herein may provide a technical solution to the technical problem pertaining to the patient's medical condition information being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). The information may be converted from the format used by the sources to the standardized format used by the artificial intelligence engine. Further, the information converted to the standardized format used by the artificial intelligence engine may be stored in a database accessed by the artificial intelligence engine when performing any of the techniques disclosed herein. The standardized information may enable generating optimal treatment plans, where the generating is based on treatment plans associated with the standardized information, monetary value amounts, and the set of constraints. The optimal treatment plans may be provided in a standardized format that can be processed by various applications (e.g., telehealth) executing on various computing devices of medical professionals and/or patients.

In some embodiments, the treatment apparatus may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a medical professional may adapt, remotely during a telemedicine session, the treatment apparatus to the needs of the patient by causing a control instruction to be transmitted from a server to treatment apparatus. Such adaptive nature may improve the results of recovery for a patient, furthering the goals of personalized medicine, and enabling personalization of the treatment plan on a per-individual basis.

FIG. 1 shows a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients.

The system data store 42 may be configured to hold data relating to billing procedures, including rules and constraints pertaining to billing codes, order, timing, insurance regimes, laws, regulations, or some combination thereof. The system data store 42 may be configured to store various billing sequences generated based on billing procedures and various parameters (e.g., monetary value amount generated, patient outcome, plan of reimbursement, fees, a payment plan for patients to pay of an amount of money owed, an amount of revenue to be paid to an insurance provider, etc.). The system data store 42 may be configured to store optimal treatment plans generated based on various treatment plans for users having similar medical conditions, monetary value amounts generated by the treatment plans, and the constraints. Any of the data stored in the system data store 42 may be accessed by an artificial intelligence engine 11 when performing any of the techniques described herein.

The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

In addition, the characteristics (e.g., personal, performance, measurement, etc.) of the people, the treatment plans followed by the people, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment apparatuses and/or computing devices over time and stored in the database 44. The characteristic data, treatment plan data, and results data may be correlated in the patient-cohort databases in the patient data store 44. The characteristics of the people may include personal information, performance information, and/or measurement information.

In addition to the historical information about other people stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another person in a particular cohort (e.g., cohort A) and the patient may be assigned to that cohort.

In some embodiments, the server 30 may execute the artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their characteristics, select treatment plans using real-time and historical data correlations involving patient cohort-equivalents, and control a treatment apparatus 70, among other things. The machine learning models 13 may be trained to generate, based on billing procedures, billing sequences and/or treatment plans tailored for various parameters (e.g., a fee to be paid to a medical professional, a payment plan for the patient to pay off an amount of money owed, a plan of reimbursement, an amount of revenue to be paid to an insurance provider, or some combination thereof). The machine learning models 13 may be trained to generate, based on constraints, optimal treatment plans tailored for various parameters (e.g., monetary value amount generated, patient outcome, risk, etc.). The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based or a real-time software platform, and it may include privacy software or protocols, and/or security software or protocols.

To train the one or more machine learning models 13, the training engine 9 may use a training data set of a corpus of the information (e.g., characteristics, medical diagnosis codes, etc.) pertaining to medical conditions of the people who used the treatment apparatus 70 to perform treatment plans, the details (e.g., treatment protocol including exercises, amount of time to perform the exercises, instructions for the patient to follow, how often to perform the exercises, a schedule of exercises, parameters/configurations/settings of the treatment apparatus 70 throughout each step of the treatment plan, etc.) of the treatment plans performed by the people using the treatment apparatus 70, the results of the treatment plans performed by the people, a set of monetary value amounts associated with the treatment plans, a set of constraints (e.g., rules pertaining to billing codes associated with the set of treatment plans, laws, regulations, etc.), a set of billing procedures (e.g., rules pertaining to billing codes, order, timing and constraints) associated with treatment plan instructions, a set of parameters (e.g., a fee to be paid to a medical professional, a payment plan for the patient to pay off an amount of money owed, a plan of reimbursement, an amount of revenue to be paid to an insurance provider, or some combination thereof, a treatment plan, a monetary value amount generated, a risk, etc.), insurance regimens, etc.

The one or more machine learning models 13 may be trained to match patterns of characteristics of a patient with characteristics of other people in assigned to a particular cohort. The term "match" may refer to an exact match, a correlative match, a substantial match, etc. The one or more machine learning models 13 may be trained to receive the characteristics of a patient as input, map the characteristics to characteristics of people assigned to a cohort, and select a treatment plan from that cohort. The one or more machine learning models 13 may also be trained to control, based on the treatment plan, the machine learning apparatus 70.

The one or more machine learning models 13 may be trained to match patterns of a first set of parameters (e.g., treatment plans for patients having a medical condition, a set of monetary value amounts associated with the treatment plans, patient outcome, and/or a set of constraints) with a second set of parameters associated with an optimal treatment plan. The one or more machine learning models 13 may be trained to receive the first set of parameters as input, map the characteristics to the second set of parameters associated with the optimal treatment plan, and select the optimal treatment plan a treatment plan. The one or more machine learning models 13 may also be trained to control, based on the treatment plan, the machine learning apparatus 70.

The one or more machine learning models 13 may be trained to match patterns of a first set of parameters (e.g., information pertaining to a medical condition, treatment plans for patients having a medical condition, a set of monetary value amounts associated with the treatment plans, patient outcomes, instructions for the patient to follow in a treatment plan, a set of billing procedures associated with the instructions, and/or a set of constraints) with a second set of parameters associated with a billing sequence and/or optimal treatment plan. The one or more machine learning models 13 may be trained to receive the first set of parameters as input, map or otherwise associate or algorithmically associate the first set of parameters to the second set of parameters associated with the billing sequence and/or optimal treatment plan, and select the billing sequence and/or optimal treatment plan for the patient. In some embodiments, one or more optimal treatment plans may be selected to be provided to a computing device of the medical professional and/or the patient. The one or more machine learning models 13 may also be trained to control, based on the treatment plan, the machine learning apparatus 70.

Different machine learning models 13 may be trained to recommend different treatment plans tailored for different parameters. For example, one machine learning model may be trained to recommend treatment plans for a maximum monetary value amount generated, while another machine learning model may be trained to recommend treatment plans based on patient outcome, or based on any combination of monetary value amount and patient outcome, or based on those and/or additional goals. Also, different machine learning models 13 may be trained to recommend different billing sequences tailored for different parameters. For example, one machine learning model may be trained to recommend billing sequences for a maximum fee to be paid to a medical professional, while another machine learning model may be trained to recommend billing sequences based on a plan of reimbursement.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

In some embodiments, the output device 54 may present a user interface that may present a recommended treatment plan, billing sequence, or the like to the patient. The user interface may include one or more graphical elements that enable the user to select which treatment plan to perform. Responsive to receiving a selection of a graphical element (e.g., "Start" button) associated with a treatment plan via the input device 54, the patient interface 50 may communicate a control signal to the controller 72 of the treatment apparatus, wherein the control signal causes the treatment apparatus 70 to begin execution of the selected treatment plan. As described below, the control signal may control, based on the selected treatment plan, the treatment apparatus 70 by causing actuation of the actuator 78 (e.g., cause a motor to drive rotation of pedals of the treatment apparatus at a certain speed), causing measurements to be obtained via the sensor 76, or the like. The patient interface 50 may communicate, via a local communication interface 68, the control signal to the treatment apparatus 70.

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment apparatus 70 may be any suitable medical, rehabilitative, therapeutic, etc. apparatus configured to be controlled distally via another computing device to treat a patient and/or exercise the patient. The treatment apparatus 70 may be an electromechanical machine including one or more weights, an electromechanical bicycle, an electromechanical spinwheel, a smart-mirror, a treadmill, or the like. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for an assistant, such as a doctor, a nurse, a physical therapist, or a technician, to remotely communicate with the patient interface 50 and/or the treatment apparatus 70. Such remote communications may enable the assistant to provide assistance or guidance to a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58. The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the assistant may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the assistant to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the assistant. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the assistant. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate treatment plans, billing sequences, and/or excluded treatment plans for patients and generate the display screens including those treatment plans, billing sequences, and/or excluded treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as an assistant remotely from any conventional office infrastructure. Such remote work may be performed, for example, where the assistant interface 94 takes the form of a computer and/or telephone. This remote work functionality may allow for work-from-home arrangements that may include part time and/or flexible work hours for an assistant.

Figure 2:
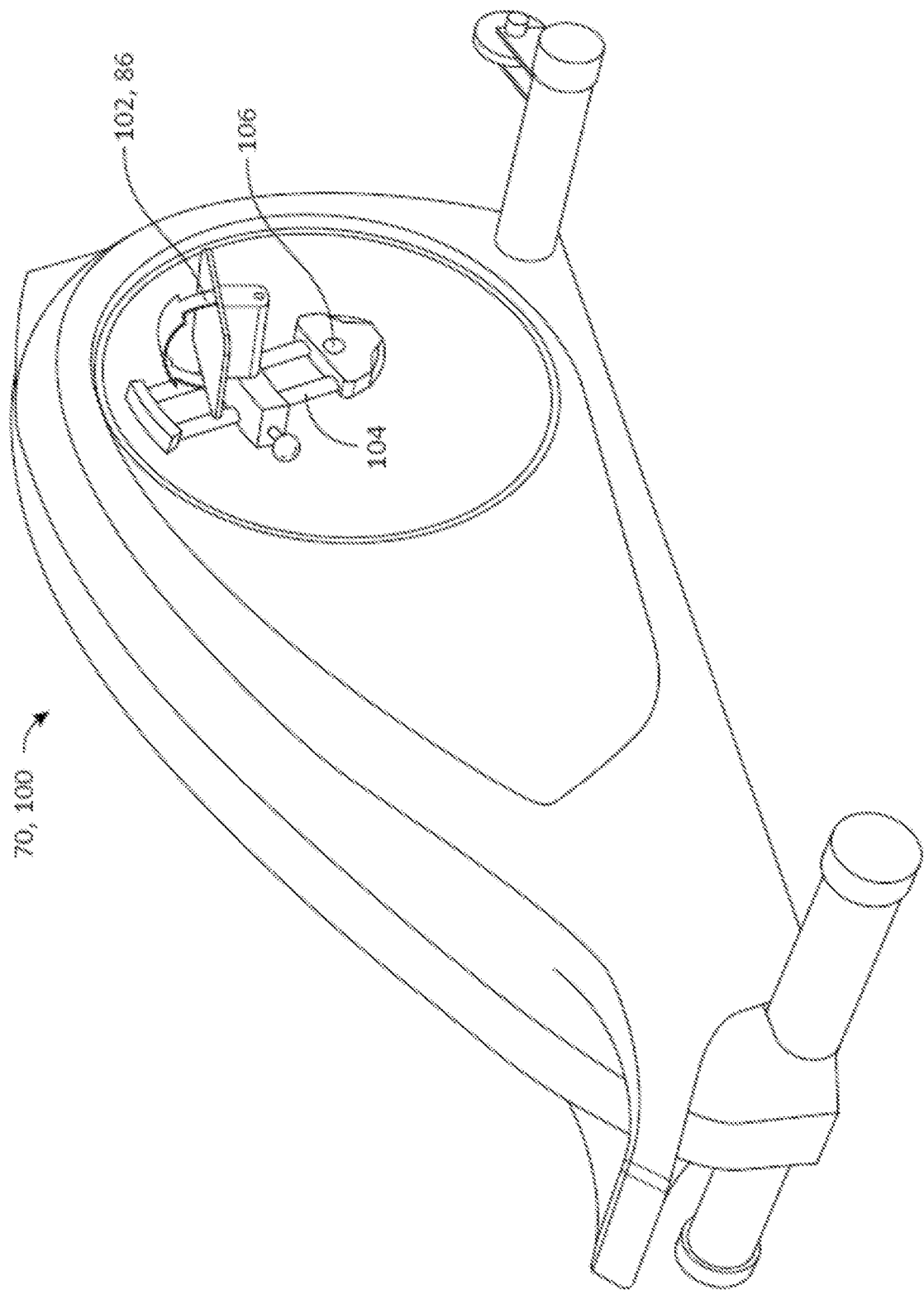
FIG. 2 shows a perspective view of an embodiment of a treatment apparatus according to the present disclosure.
Figure 3:
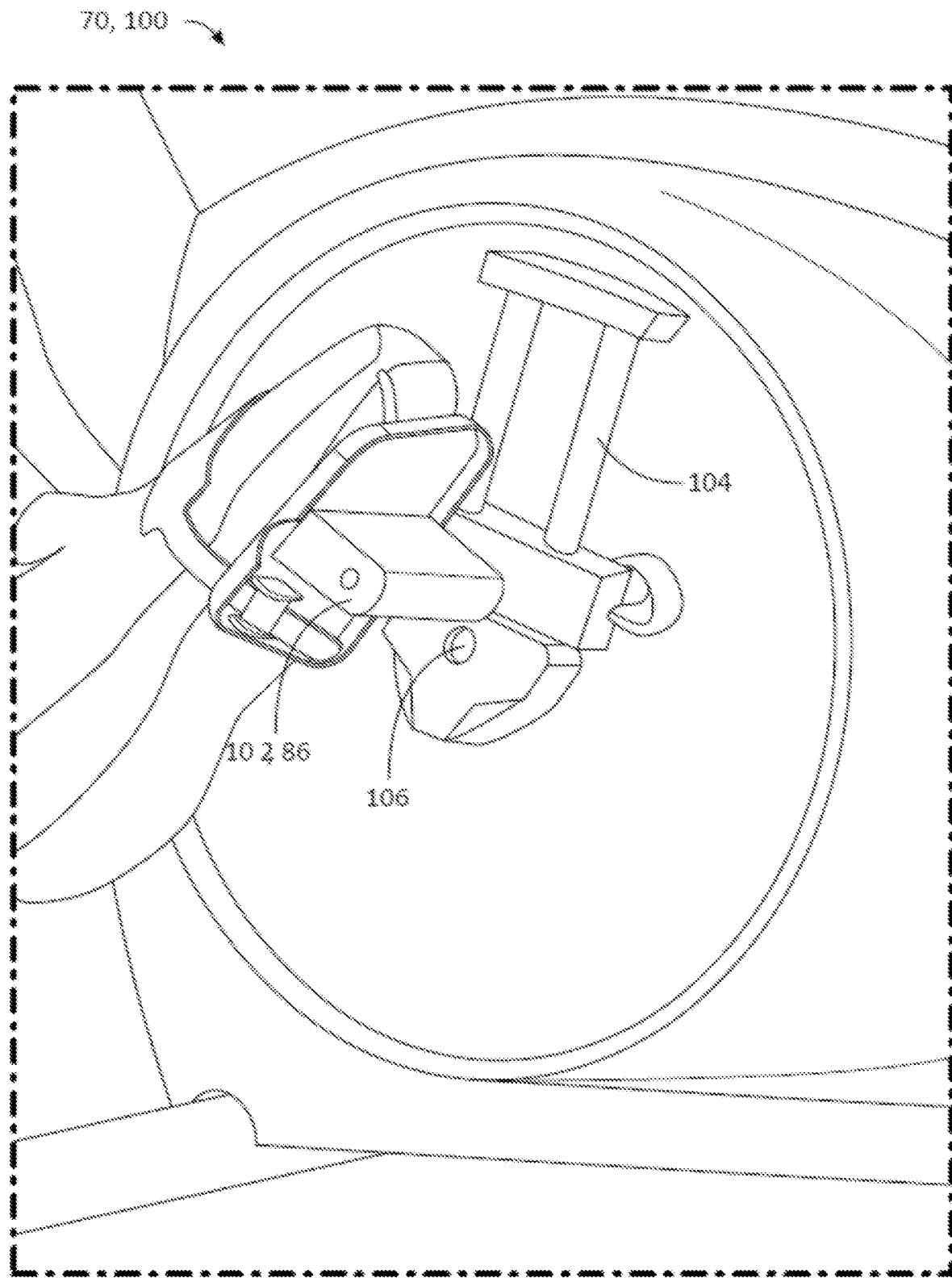
FIG. 3 shows a perspective view of a pedal of the treatment apparatus of FIG. 2 according to the present disclosure.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
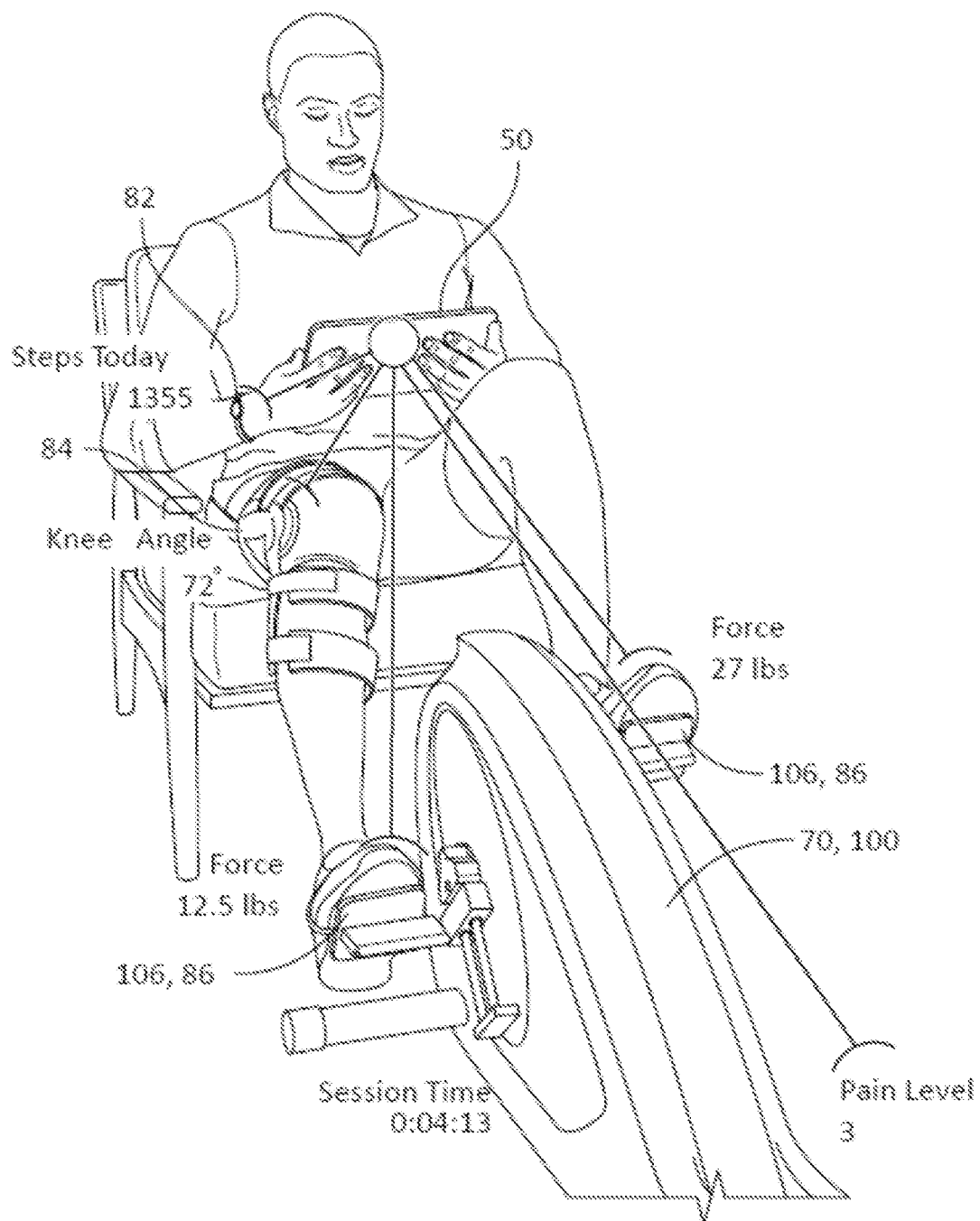
FIG. 4 shows a perspective view of a person using the treatment apparatus of FIG. 2 according to the present disclosure.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

Figure 5:
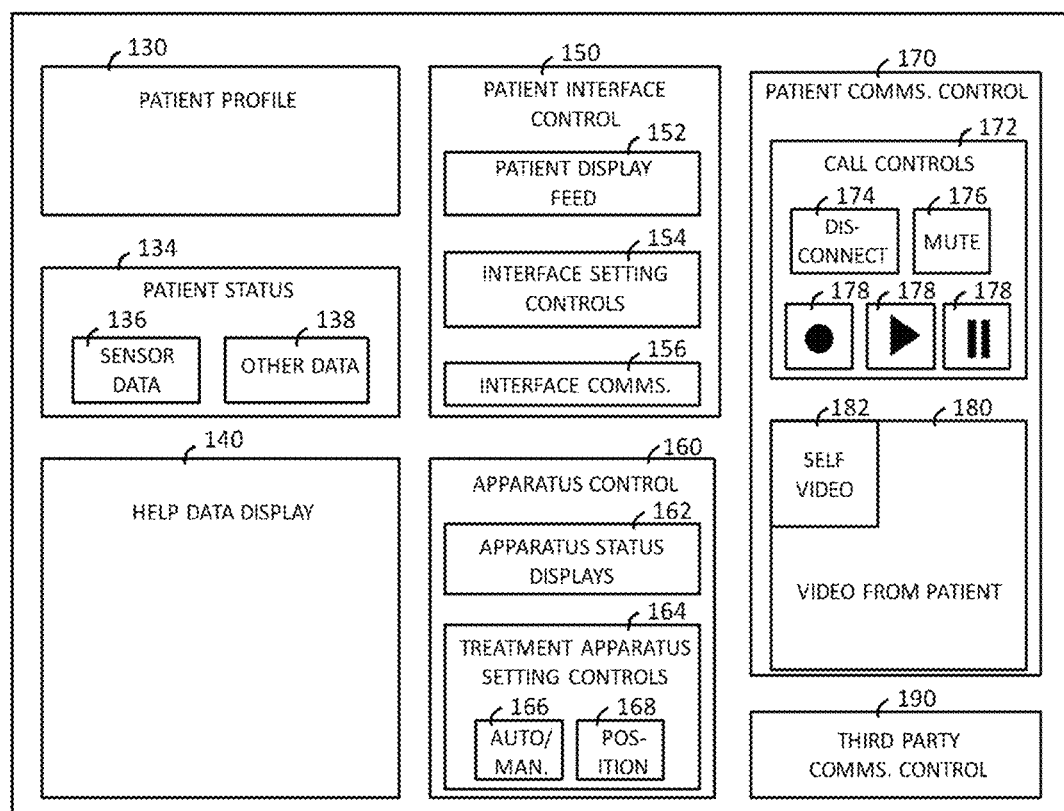
FIG. 5 shows an example embodiment of an overview display of an assistant interface according to the present disclosure.

FIG. 5 is an example embodiment of an overview display 120 of the assistant interface 94. Specifically, the overview display 120 presents several different controls and interfaces for the assistant to remotely assist a patient with using the patient interface 50 and/or the treatment apparatus 70. This remote assistance functionality may also be called telemedicine or telehealth.

Specifically, the overview display 120 includes a patient profile display 130 presenting biographical information regarding a patient using the treatment apparatus 70. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the assistant's need for that information. For example, a medical professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment apparatus 70. Such treatment plan information may be limited to an assistant who is a medical professional, such as a doctor or physical therapist. For example, a medical professional assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended treatment plans and/or excluded treatment plans may be presented in the patient profile display 130 to the assistant. The one or more recommended treatment plans and/or excluded treatment plans may be generated by the artificial intelligence engine 11 of the server 30 and received from the server 30 in real-time during, inter alia, a telemedicine or telehealth session. An example of presenting the one or more recommended treatment plans and/or ruled-out treatment plans is described below with reference to FIG. 7.

In some embodiments, one or more treatment plans and/or billing sequences associated with the treatment plans may be presented in the patient profile display 130 to the assistant. The one or more treatment plans and/or billing sequences associated with the treatment plans may be generated by the artificial intelligence engine 11 of the server 30 and received from the server 30 in real-time during, inter alia, a telehealth session. An example of presenting the one or more treatment plans and/or billing sequences associated with the treatment plans is described below with reference to FIG. 9.

In some embodiments, one or more treatment plans and associated monetary value amounts generated, patient outcomes, and risks associated with the treatment plans may be presented in the patient profile display 130 to the assistant. The one or more treatment plans and associated monetary value amounts generated, patient outcomes, and risks associated with the treatment plans may be generated by the artificial intelligence engine 11 of the server 30 and received from the server 30 in real-time during, inter alia, a telehealth session. An example of presenting the one or more treatment plans and associated monetary value amounts generated, patient outcomes, and risks associated with the treatment plans is described below with reference to FIG. 12.

The example overview display 120 shown in FIG. 5 also includes a patient status display 134 presenting status information regarding a patient using the treatment apparatus. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the assistant to use in determining a root cause and/or solution to a patient's problem. In some embodiments, the assistant interface 94 may present two or more help data displays 140, which may be the same or different, for simultaneous presentation of help data for use by the assistant. for example, a first help data display may be used to present a troubleshooting flowchart to determine the source of a patient's problem, and a second help data display may present script information for the assistant to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98b. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the assistant to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the assistant to remotely view and/or control the patient interface 50. For example, the patient interface setting control 154 may enable the assistant to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the assistant to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the assistant to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the assistant to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99b. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99 for changing an operating parameter of the treatment apparatus 70, (e.g., a pedal radius setting, a resistance setting, a target RPM, etc.). The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the assistant may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the assistant to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the assistant while the assistant uses the assistant interface 94. Alternatively or additionally, the audio and/or audiovisual communications may include communications with a third party. For example, the system 10 may enable the assistant to initiate a 3-way conversation regarding use of a particular piece of hardware or software, with the patient and a subject matter expert, such as a medical professional or a specialist. The example patient communications control 170 shown in FIG. 5 includes call controls 172 for the assistant to use in managing various aspects of the audio or audiovisual communications with the patient. The call controls 172 include a disconnect button 174 for the assistant to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session. The call controls 172 also include a video feed display 180 for presenting still and/or video images from the patient interface 50, and a self-video display 182 showing the current image of the assistant using the assistant interface. The self-video display 182 may be presented as a picture-in-picture format, within a section of the video feed display 180, as shown in FIG. 5. Alternatively or additionally, the self-video display 182 may be presented separately and/or independently from the video feed display 180.

The example overview display 120 shown in FIG. 5 also includes a third party communications control 190 for use in conducting audio and/or audiovisual communications with a third party. The third party communications control 190 may take the form of a portion or region of the overview display 120, as shown in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a medical professional or a specialist. The third party communications control 190 may include conference calling capability for the third party to simultaneously communicate with both the assistant via the assistant interface 94, and with the patient via the patient interface 50. For example, the system 10 may provide for the assistant to initiate a 3-way conversation with the patient and the third party.

Figure 6:
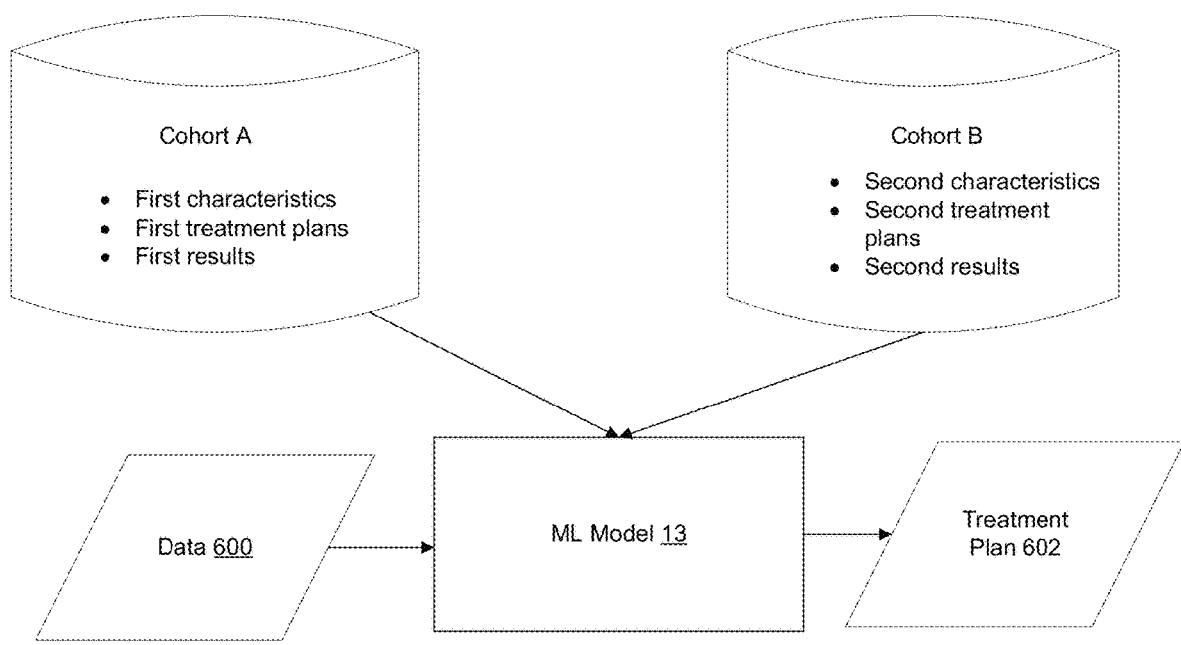
FIG. 6 shows an example block diagram of training a machine learning model to output, based on data pertaining to the patient, a treatment plan for the patient according to the present disclosure.

FIG. 6 shows an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the treatment apparatus 70 for 30 minutes 5 times a week for 3 weeks, wherein values for the properties, configurations, and/or settings of the treatment apparatus 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan 602. In some embodiments, the machine learning model 13 may be trained to output one or more excluded treatment plans that should not be performed by the new patient.

Figure 7:
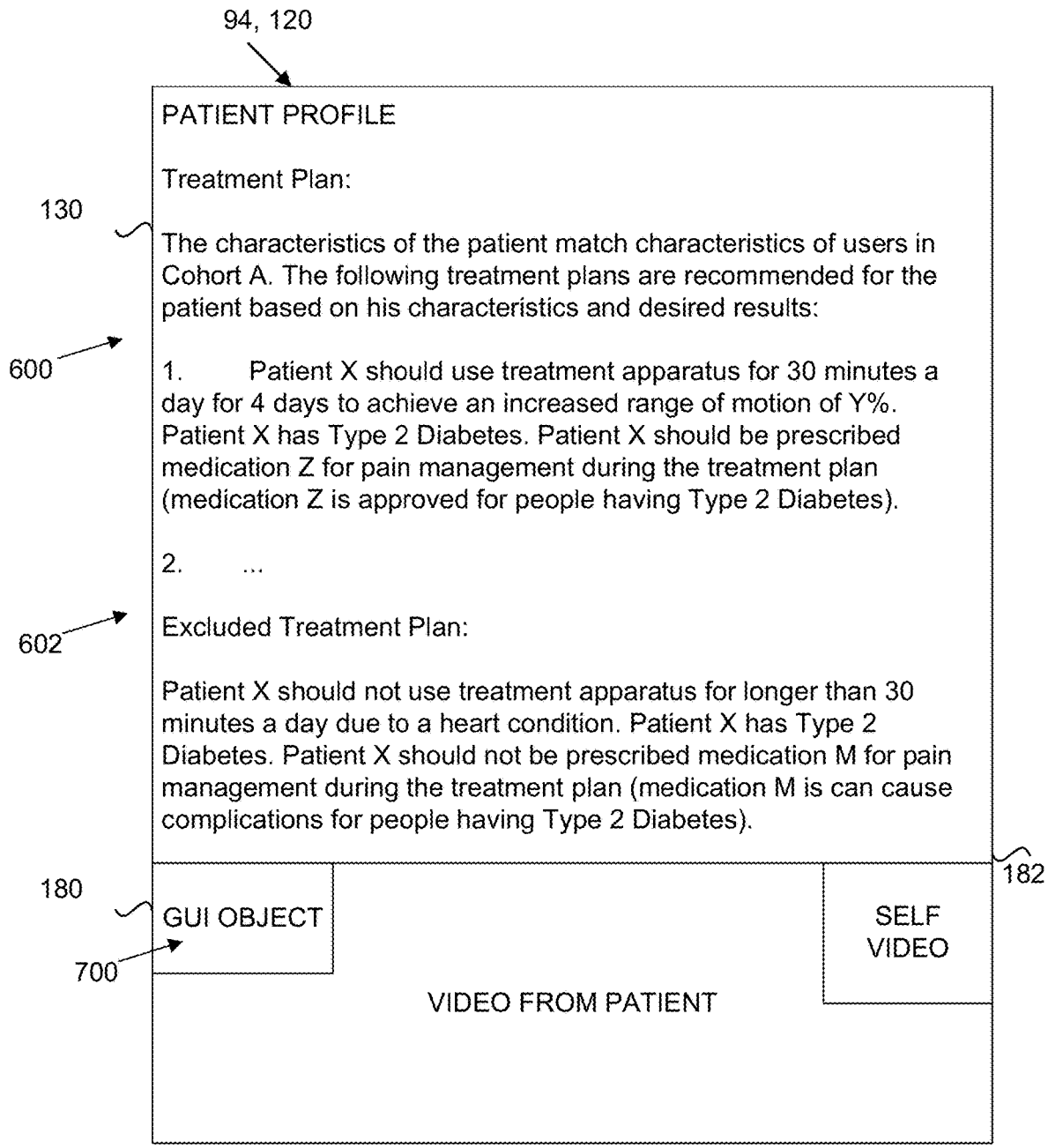
FIG. 7 shows an embodiment of an overview display of the assistant interface presenting recommended treatment plans and excluded treatment plans in real-time during a telemedicine session according to the present disclosure.

FIG. 7 shows an embodiment of an overview display 120 of the assistant interface 94 presenting recommended treatment plans and excluded treatment plans in real-time during a telemedicine session according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

The assistant (e.g., medical professional) using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the medical professional to share, in real-time or near real-time during the telemedicine session, the recommended treatment plans and/or the excluded treatment plans with the patient on the patient interface 50. The medical professional may select the GUI object 700 to share the recommended treatment plans and/or the excluded treatment plans. As depicted, another portion of the overview display 120 includes the patient profile display 130.

The patient profile display 130 is presenting two example recommended treatment plans 600 and one example excluded treatment plan 602. As described herein, the treatment plans may be recommended in view of characteristics of the patient being treated. To generate the recommended treatment plans 600 the patient should follow to achieve a desired result, a pattern between the characteristics of the patient being treated and a cohort of other people who have used the treatment apparatus 70 to perform a treatment plan may be matched by one or more machine learning models 13 of the artificial intelligence engine 11. Each of the recommended treatment plans may be generated based on different desired results.

For example, as depicted, the patient profile display 130 presents "The characteristics of the patient match characteristics of users in Cohort A. The following treatment plans are recommended for the patient based on his characteristics and desired results." Then, the patient profile display 130 presents recommended treatment plans from cohort A, and each treatment plan provides different results.

As depicted, treatment plan "A" indicates "Patient X should use treatment apparatus for 30 minutes a day for 4 days to achieve an increased range of motion of Y %; Patient X has Type 2 Diabetes; and Patient X should be prescribed medication Z for pain management during the treatment plan (medication Z is approved for people having Type 2 Diabetes)." Accordingly, the treatment plan generated achieves increasing the range of motion of Y %. As may be appreciated, the treatment plan also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome. This specific example and all such examples elsewhere herein are not intended to limit in any way the generated treatment plan from recommending multiple medications, or from handling the acknowledgement, view, diagnosis and/or treatment of comorbid conditions or diseases.

Recommended treatment plan "B" may specify, based on a different desired result of the treatment plan, a different treatment plan including a different treatment protocol for a treatment apparatus, a different medication regimen, etc.

As depicted, the patient profile display 130 may also present the excluded treatment plans 602. These types of treatment plans are shown to the assistant using the assistant interface 94 to alert the assistant not to recommend certain portions of a treatment plan to the patient. For example, the excluded treatment plan could specify the following: "Patient X should not use treatment apparatus for longer than 30 minutes a day due to a heart condition; Patient X has Type 2 Diabetes; and Patient X should not be prescribed medication M for pain management during the treatment plan (in this scenario, medication M can cause complications for people having Type 2 Diabetes). Specifically, the excluded treatment plan points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

The assistant may select the treatment plan for the patient on the overview display 120. For example, the assistant may use an input peripheral (e.g., mouse, touchscreen, microphone, keyboard, etc.) to select from the treatment plans 600 for the patient. In some embodiments, during the telemedicine session, the assistant may discuss the pros and cons of the recommended treatment plans 600 with the patient.

In any event, the assistant may select the treatment plan for the patient to follow to achieve the desired result. The selected treatment plan may be transmitted to the patient interface 50 for presentation. The patient may view the selected treatment plan on the patient interface 50. In some embodiments, the assistant and the patient may discuss during the telemedicine session the details (e.g., treatment protocol using treatment apparatus 70, diet regimen, medication regimen, etc.) in real-time or in near real-time. In some embodiments, the server 30 may control, based on the selected treatment plan and during the telemedicine session, the treatment apparatus 70 as the user uses the treatment apparatus 70.

Figure 8:
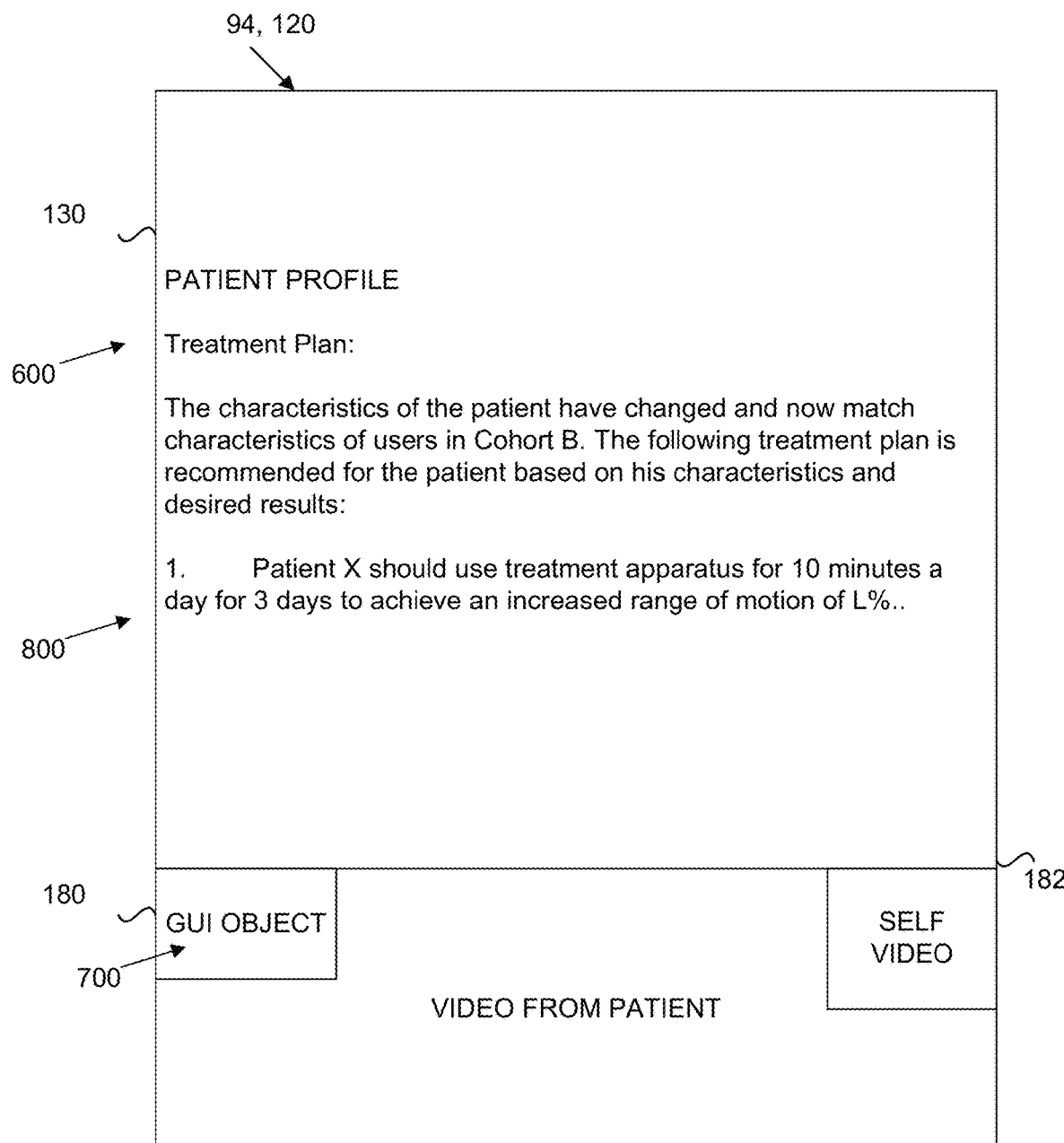
FIG. 8 shows an embodiment of the overview display of the assistant interface presenting, in real-time during a telemedicine session, recommended treatment plans that have changed as a result of patient data changing according to the present disclosure.

FIG. 8 shows an embodiment of the overview display 120 of the assistant interface 94 presenting, in real-time during a telemedicine session, recommended treatment plans that have changed as a result of patient data changing according to the present disclosure. As may be appreciated, the treatment apparatus 70 and/or any computing device (e.g., patient interface 50) may transmit data while the patient uses the treatment apparatus 70 to perform a treatment plan. The data may include updated characteristics of the patient. For example, the updated characteristics may include new performance information and/or measurement information. The performance information may include a speed of a portion of the treatment apparatus 70, a range of motion achieved by the patient, a force exerted on a portion of the treatment apparatus 70, a heartrate of the patient, a blood pressure of the patient, a respiratory rate of the patient, and so forth.

In one embodiment, the data received at the server 30 may be input into the trained machine learning model 13, which may determine that the characteristics indicate the patient is on track for the current treatment plan. Determining the patient is on track for the current treatment plan may cause the trained machine learning model 13 to adjust a parameter of the treatment apparatus 70. The adjustment may be based on a next step of the treatment plan to further improve the performance of the patient.

In one embodiment, the data received at the server 30 may be input into the trained machine learning model 13, which may determine that the characteristics indicate the patient is not on track (e.g., behind schedule, not able to maintain a speed, not able to achieve a certain range of motion, is in too much pain, etc.) for the current treatment plan or is ahead of schedule (e.g., exceeding a certain speed, exercising longer than specified with no pain, exerting more than a specified force, etc.) for the current treatment plan. The trained machine learning model 13 may determine that the characteristics of the patient no longer match the characteristics of the patients in the cohort to which the patient is assigned. Accordingly, the trained machine learning model 13 may reassign the patient to another cohort that includes qualifying characteristics the patient's characteristics. As such, the trained machine learning model 13 may select a new treatment plan from the new cohort and control, based on the new treatment plan, the treatment apparatus 70.

In some embodiments, prior to controlling the treatment apparatus 70, the server 30 may provide the new treatment plan 800 to the assistant interface 94 for presentation in the patient profile 130. As depicted, the patient profile 130 indicates "The characteristics of the patient have changed and now match characteristics of users in Cohort B. The following treatment plan is recommended for the patient based on his characteristics and desired results." Then, the patient profile 130 presents the new treatment plan 800 ("Patient X should use treatment apparatus for 10 minutes a day for 3 days to achieve an increased range of motion of L %" The assistant (medical professional) may select the new treatment plan 800, and the server 30 may receive the selection. The server 30 may control the treatment apparatus 70 based on the new treatment plan 800. In some embodiments, the new treatment plan 800 may be transmitted to the patient interface 50 such that the patient may view the details of the new treatment plan 800.

Figure 9:
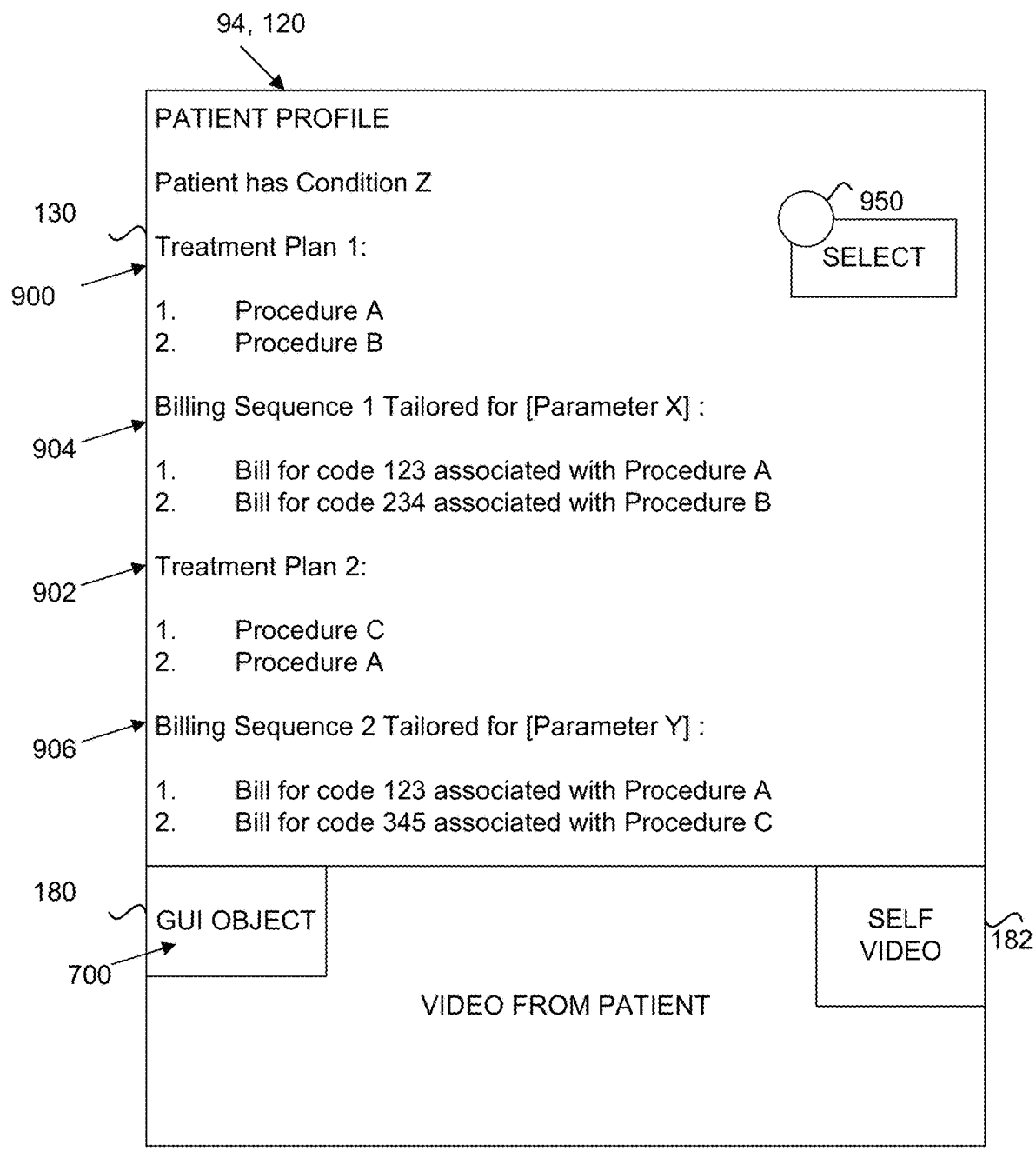
FIG. 9 shows an embodiment of the overview display of the assistant interface presenting, in real-time during a telemedicine session, treatment plans and billing sequences tailored for certain parameters according to the present disclosure.

FIG. 9 shows an embodiment of the overview display 120 of the assistant interface 94 presenting, in real-time during a telemedicine session, treatment plans and billing sequences tailored for certain parameters according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182. In some embodiments, the same treatment plans and billing sequences may be presented in a display screen 54 of the patient interface 50. In some embodiments, the treatment plans and billing sequences may be presented simultaneously, in real-time or near real-time, during a telemedicine or telehealth session, on both the display screen 54 of the patient interface 50 and the display screen 24 of the assistant interface 94.

The assistant (e.g., medical professional) using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the medical professional to share, in real-time or near real-time during the telemedicine session, the treatment plans and/or the billing sequences with the patient on the patient interface 50. The medical professional may select the GUI object 700 to share the treatment plans and/or the billing sequences. As depicted, another portion of the overview display 120 includes the patient profile display 130.

The patient profile display 130 is presenting two example treatment plans and two example billing sequences. Treatment plans 900 and 902 may be generated based on information (e.g., medical diagnosis code) pertaining to a condition of the patient. Treatment plan 900 corresponds to billing sequence 904, and treatment plan 902 corresponds to billing sequence 906. The generated billing sequences 904 and 906 and the treatment plans 900 and 902 comply with a set of billing procedures including rules pertaining to billing codes, order, timing, and constraints (e.g., laws, regulations, etc.). As described herein, each of the respective the billing sequences 904 and 906 may be generated based on a set of billing procedures associated with at least a portion of instructions included in each of the respective treatment plans 900 and 902. Further, each of the billing sequences 904 and 906 and/or treatment plans 900 and 902 may be tailored according to a certain parameter (e.g., a fee to be paid to a medical professional, a payment plan for the patient to pay off an amount of money owed, a plan of reimbursement, a monetary value amount to be paid to an insurance provider, or some combination thereof). In some embodiments, the monetary value amount "to be paid" may be inclusive to any means of settling an account with an insurance provider (e.g., payment of monetary, issuance of credit).

Each of the respective treatment plans 900 and 902 may include one or more procedures to be performed on the patient based on the information pertaining to the medical condition of the patient. Further, each of the respective billing sequences 904 and 906 may include an order for how the procedures are to be billed based on the billing procedures and one or more parameters.

For example, as depicted, the patient profile display 130 presents "Patient has Condition Z", where condition Z may be associated with information of the patient including a particular medical diagnosis code received from an EMR system. Based on the information, the treatment plans 900 and 906 each include procedures relevant to be performed for the Condition Z. The patient profile 130 presents "Treatment Plan 1: 1. Procedure A; 2. Procedure B". Each of the procedures may specify one or more instructions for performing the procedures, and each of the one or more instructions may be associated with a particular billing code or codes. Then, the patient profile display 130 presents the billing sequence 904 generated, based on the billing procedures and one or more parameters, for at least a portion of the one or more instructions included in the treatment plan 900. The patient profile display 130 presents "Billing Sequence 1 Tailored for [Parameter X]: 1. Bill for code 123 associated with Procedure A; 2. Bill for code 234 associated with Procedure B". It should be noted that [Parameter X] may be any suitable parameter, such as a fee to be paid to a medical professional, a payment plan for the patient to pay off an amount of money owed, a plan of reimbursement, a monetary value amount to be paid to an insurance provider, or some combination thereof.

Further, the patient profile 130 also presents the treatment plan 902 and presents "Treatment Plan 2: 1. Procedure C; 2. Procedure A". Each of the procedures may specify one or more instructions for performing the procedures, and each of the one or more instructions may be associated with a particular billing code. Then, the patient profile display 130 presents the billing sequence 906 generated, based on the billing procedures and one or more parameters, for at least a portion of the one or more instructions included in the treatment plan 902. The patient profile display 130 presents "Billing Sequence 2 Tailored for [Parameter Y]: 1. Bill for code 345 associated with Procedure C; 2. Bill for code 123 associated with Procedure A". It should be noted that [Parameter Y] may be any suitable parameter, such as a fee to be paid to a medical professional, a payment plan for the patient to pay off an amount of money owed, a plan of reimbursement, a monetary value amount to be paid to an insurance provider, or some combination thereof. It should also be noted that in the depicted example [Parameter X] and [Parameter Y] are different parameters.

As should be appreciated, the billing sequence 904 and 906 includes a different order for billing the procedures included in the respective treatment plans 900 902, and each of the billing sequences 904 and 906 complies with the billing procedures. The billing sequence 904 may have been tailored for [Parameter X] (e.g., a fee to be paid to a medical professional) and the billing sequence 906 may have been tailored for [Parameter Y] (e.g., a plan of reimbursement).

The order of performing the procedures for the treatment plan 902 specifies performing Procedure C first and then Procedure A. However, the billing sequence 906 specifies billing for the code 123 associated with Procedure A first and then billing for the code 345 associated with Procedure C. Such a billing sequence 906 may have been dictated by the billing procedures. For example, although Procedure A is performed second, a law, regulation, or the like may dictate that Procedure A be billed before any other procedure.

Further, as depicted, a graphical element (e.g., button for "SELECT") may be presented in the patient profile display 130. Although just one graphical element is presented, any suitable number of graphical elements for selecting a treatment plan and/or billing sequence may be presented in the patient profile display 130. As depicted, a user (e.g., medical professional or patient) uses an input peripheral (e.g., mouse, keyboard, microphone, touchscreen) to select (as represented by circle 950) the graphical element associated with the treatment plan 900 and billing sequence 904. The medical professional may prefer to receive a certain fee and the billing sequence 904 is optimized based on [Parameter X] (e.g., a fee to be paid to the medical professional, as previously discussed). Accordingly, the assistant interface 94 may transmit a control signal to the treatment apparatus 70 to control, based on the treatment plan 900, operation of the treatment apparatus 70. In some embodiments, the patient may select the treatment plan from the display screen 54 and the patient interface 50 may transmit a control signal to the treatment apparatus 70 to control, based on the selected treatment plan, operation of the treatment apparatus 70.

Figure 10:
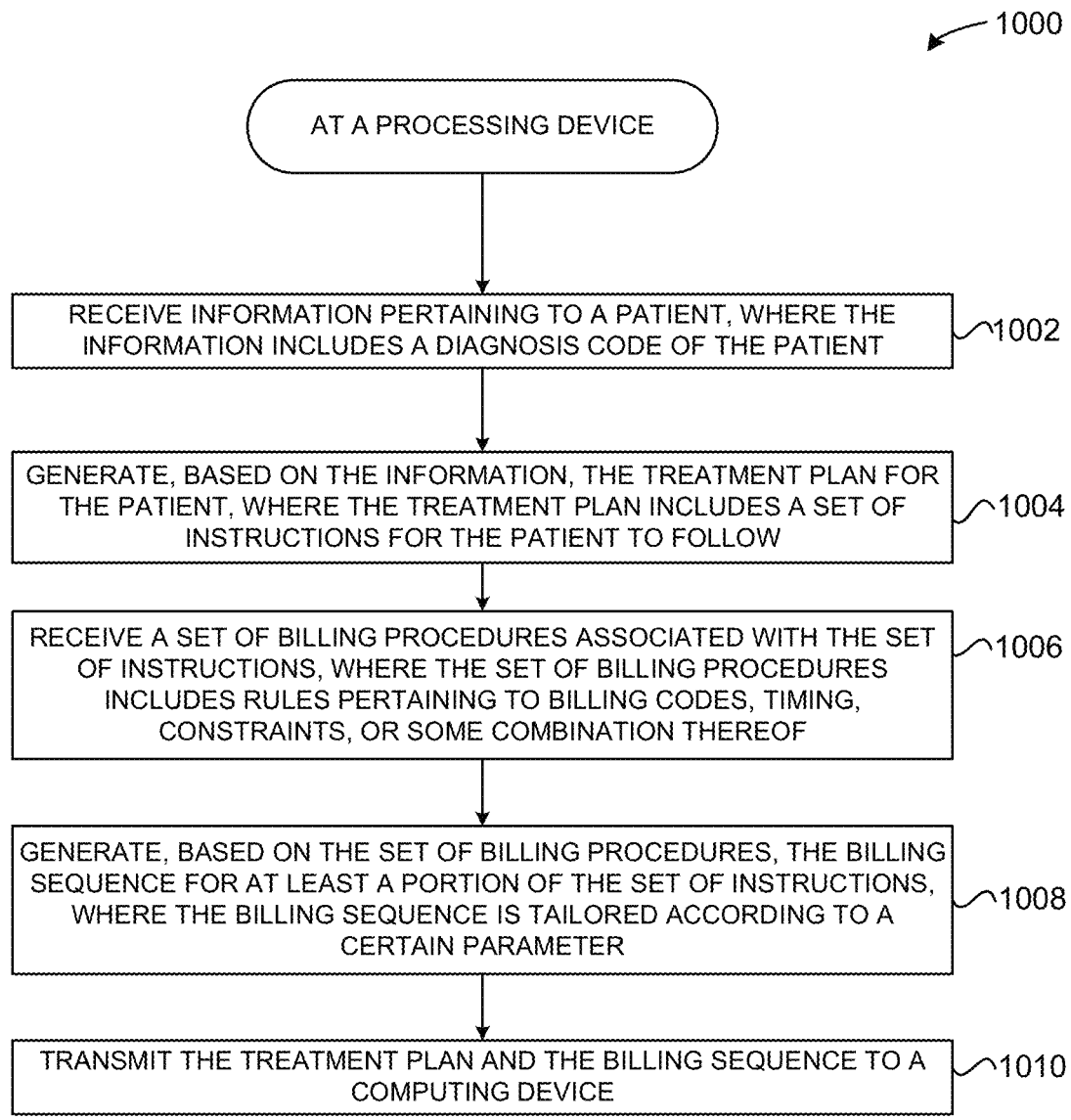
FIG. 10 shows an example embodiment of a method for generating, based on a set of billing procedures, a billing sequence tailored for a particular parameter, where the billing sequence pertains to a treatment plan according to the present disclosure.

FIG. 10 shows an example embodiment of a method 1000 for generating, based on a set of billing procedures, a billing sequence tailored for a particular parameter, where the billing sequence pertains to a treatment plan according to the present disclosure. The method 1000 is performed by processing logic that may include hardware (circuitry, dedicated logic, etc.), software (such as is run on a general-purpose computer system or a dedicated machine), or a combination of both. The method 1000 and/or each of its individual functions, routines, other methods, scripts, subroutines, or operations may be performed by one or more processors of a computing device (e.g., any component of FIG. 1, such as server 30 executing the artificial intelligence engine 11). In certain implementations, the method 1000 may be performed by a single processing thread. Alternatively, the method 1000 may be performed by two or more processing threads, each thread implementing one or more individual functions, routines, other methods, scripts, subroutines, or operations of the methods.

For simplicity of explanation, the method 1000 is depicted and described as a series of operations. However, operations in accordance with this disclosure can occur in various orders and/or concurrently, and/or with other operations not presented and described herein. For example, the operations depicted in the method 1000 may occur in combination with any other operation of any other method disclosed herein. Furthermore, not all illustrated operations may be required to implement the method 1000 in accordance with the disclosed subject matter. In addition, those skilled in the art will understand and appreciate that the method 1000 could alternatively be represented as a series of interrelated states via a state diagram, a directed graph, a deterministic finite state automaton, a non-deterministic finite state automaton, a Markov diagram, or events.

At 1002, the processing device may receive information pertaining to a patient. The information may include a medical diagnosis code (DRG, ICD-9, ICD-10, etc.) associated with the patient. The information may also include characteristics of the patient, such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, the body part used to exert the amount of force, the tendons, ligaments, muscles and other body parts associated with or connected to the body part, a range of motion achieved on the treatment apparatus, a movement speed of a portion of the treatment apparatus, an indication of a plurality of pain levels using the treatment apparatus, or some combination thereof. The measurement information may include, e.g., a vital sign, a respiration rate, a heartrate, a temperature, a blood pressure, or some combination thereof. It may be desirable to process the characteristics of a multitude of patients, the treatment plans performed for those patients, and the results of the treatment plans for those patients.

At 1004, the processing device may generate, based on the information, a treatment plan for the patient. The treatment plan may include a set of instructions for the patient to follow (e.g., for rehabilitation, prehabilitation, post-habilitation, etc.). In some embodiments, the treatment plan may be generated by comparing and matching the information of the patient with information of other patients. In some embodiments, the treatment plan may pertain to habilitation, prehabilitation, rehabilitation, post-habilitation, exercise, strength training, endurance training, weight loss, weight gain, flexibility, pliability, or some combination thereof. In some embodiments, the set of instructions may include a set of exercises for the patient to perform, an order for the set of exercises, a frequency for performing the set of exercises, a diet program, a sleep regimen, a set of procedures to perform on the patient, an order for the set of procedures, a medication regimen, a set of sessions for the patient, or some combination thereof.

At 1006, the processing device may receive a set of billing procedures associated with the set of instructions. The set of billing procedures may include rules pertaining to billing codes, timing, order, insurance regimens, constraints, or some combination thereof. In some embodiments, the constraints may include constraints set forth in regulations, laws, or some combination thereof. The rules pertaining to the billing codes may specify exact billing codes for procedures. The billing codes may be standardized and mandated by certain regulatory agencies and/or systems. A certain billing code may be unique to a certain procedure.

The rules pertaining to the timing information may specify when certain procedures and/or associated billing codes may be billed. The timing information may also specify a length of time from when a procedure is performed until the procedure can be billed, a periodicity that certain procedures may be billed, a frequency that certain procedures may be billed, and so forth.

The rules pertaining to the order information may specify an order in which certain procedures and/or billing codes may be billed to the patient. For example, the rules may specify that a certain procedure cannot be billed until another procedure is billed.

The rules pertaining to the insurance regimens may specify what amount and/or percentage the insurance provider pays based on the insurance benefits of the patient, when the insurance provider distributes payments, and the like.

The rules pertaining to the constraints may include laws and regulations of medical billing. For example, the Health Insurance Portability and Accountability Act (HIPAA) includes numerous medical billing laws and regulations. In the European Union, the General Protection Data Regulation (GDPR) would impose certain constraints. One of the laws and regulations is patient confidentiality, which makes it necessary for each and every medical practice to create safeguards against the leaking of confidential patient information. Another of the laws and regulations is the use of ICD-10 codes, which allow for more specificity in reporting of patient diagnoses. Other laws and regulations, in certain jurisdictions, may include requirements to pseudonymize, pseudonymise, anonymize or anonymise (the terms can have different meanings in different countries and jurisdictions) data subject (i.e., patient) personally identifying information (PII) or personal health identifying information (PHI).

Another law and regulation pertains to balance billing. When a healthcare provider signs a contract with an insurance company, the healthcare provider agrees to take a certain percentage or payment amount for specific services. The amount the healthcare provider bills over the agreed upon amount with the insurance provider must be written off by the healthcare provider's office. That is, the healthcare provider cannot bill the patient for any amount over the negotiated rate. If, nevertheless, a healthcare provider does this, it is referred to as balance billing, which is illegal per the contract with the insurance company.

Further, medical billing fraud is also specified as being illegal by HIPAA. Medical billing fraud may refer to a healthcare provider's office knowingly billing for services that were not performed, or that are inaccurately represented or described.

At 1008, the processing device may generate, based on the set of billing procedures, a billing sequence for at least a portion of the set of instructions included in the treatment plan. Just a portion of the total number of instructions may be accounted for in the billing sequence because some of the instructions may not yet have been completed or may still be completed in the future. However, if all the instructions included in the treatment plan are completed, then the billing sequence may be generated for all of the instructions. The billing sequence may be tailored according to a certain parameter. The parameter may be a fee to be paid to a medical professional, a payment plan for the patient to pay off an amount of money owed, a plan of reimbursement, a monetary value amount to be paid to an insurance provider, or some combination thereof.

At 1010, the processing device may transmit the treatment plan and the billing sequence to a computing device. The computing device may be any of the interfaces described with reference to FIG. 1. For example, the treatment plan and the billing sequence may be transmitted to an assistant interface 94 and/or a patient interface 50.

In some embodiments, the processing device may cause presentation, in real-time or near real-time during a telemedicine session with a computing device of the patient, of the treatment plan and the billing sequence on a computing device of the medical professional. Further, the processing device may cause presentation, in real-time or near real-time during a telemedicine session with the computing device of the medical professional, of the treatment plan and the billing sequence on the computing device of the medical professional.

In some embodiments, the processing device may control, based on the treatment plan, the treatment apparatus 70 used by the patient to perform the treatment plan. For example, the processing device may transmit a control signal to cause a range of motion of the pedals 102 to adjust (e.g., by electromechanically adjusting the pedals 102 attached to the pedal arms 104 inwardly or outwardly on the axle 106) to a setting specified in the treatment plan. In some embodiments, and as further described herein, a patient may view the treatment plan and/or the billing sequence and select to initiate the treatment plan using the patient interface 50. In some embodiments, and as further described herein, an assistant (e.g., medical professional) may view the treatment plan and/or the billing sequence and, using the assistant interface 94, select to initiate the treatment plan. In such an embodiment, the treatment apparatus 70 may be distally controlled via a remote computing device (e.g., server 30, assistant interface 94, etc.). For example, the remote computing device may transmit one or more control signals to the controller 72 of the treatment apparatus 70 to cause the controller 72 to execute instructions based on the control signals. By executing the instructions, the controller 72 may control various parts (e.g., pedals, motor, etc.) of the treatment apparatus 70 in real-time or near real-time while the patient uses the treatment apparatus 70.

In some embodiments, the treatment plan, including the configurations, settings, range of motion settings, pain level, force settings, speed settings, etc. of the treatment apparatus 70 for various exercises, may be transmitted to the controller of the treatment apparatus 70. In one example, if the user provides an indication, via the patient interface 50, that he is experiencing a high level of pain at a particular range of motion, the controller may receive the indication. Based on the indication, the controller may electronically adjust the range of motion of the pedal 102 by adjusting the pedal inwardly or outwardly via one or more actuators, hydraulics, springs, electric, mechanical, optical, opticoelectric or electromechanical motors, or the like. When the user indicates certain pain levels during an exercise, the treatment plan may define alternative range of motion settings for the pedal 102. Accordingly, once the treatment plan is uploaded to the controller of the treatment apparatus 70, the treatment apparatus may be self-functioning. It should be noted that the patient (via the patient interface 50) and/or the assistant (via the assistant interface 94) may override any of the configurations or settings of the treatment apparatus 70 at any time.

For example, the patient may use the patient interface 50 to cause the treatment apparatus 70 to immediately stop, if so desired.

Figure 11:
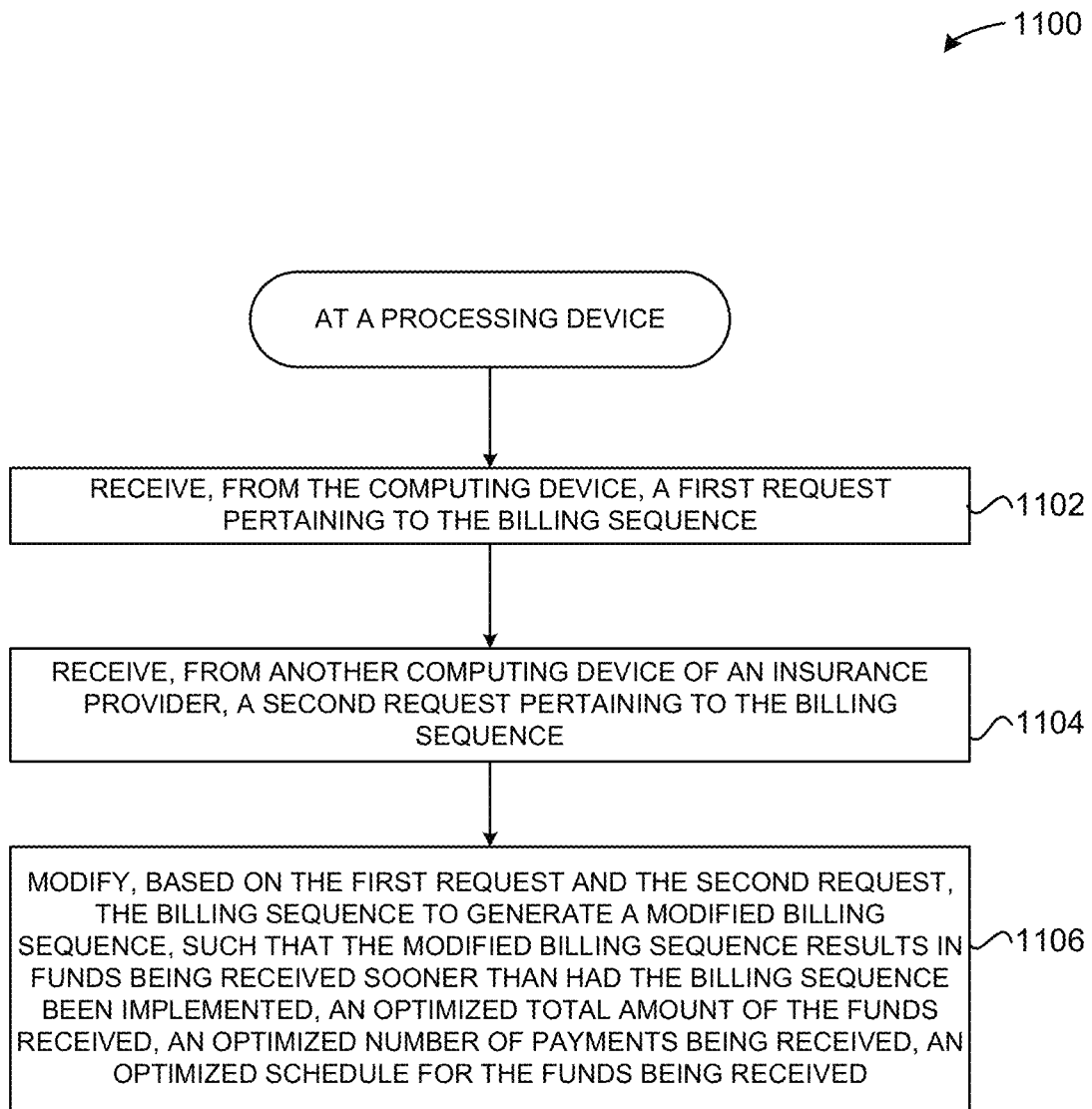
FIG. 11 shows an example embodiment of a method for receiving requests from computing devices and modifying the billing sequence based on the requests according to the present disclosure.

FIG. 11 shows an example embodiment of a method 1100 for receiving requests from computing devices and modifying the billing sequence based on the requests according to the present disclosure. Method 1100 includes operations performed by processors of a computing device (e.g., any component of FIG. 1, such as server 30 executing the artificial intelligence engine 11). In some embodiments, one or more operations of the method 1100 are implemented in computer instructions stored on a memory device and executed by a processing device. The method 1100 may be performed in the same or in a similar manner as described above in regard to method 1000. The operations of the method 1100 may be performed in some combination with any of the operations of any of the methods described herein.

At 1102, the processing device may receive, from a computing device, a first request pertaining to the billing sequence. The request may be received from a computing device of a medical professional. The request may specify that the medical professional desires instant payment of his or her portion of the bills included in the billing sequence, funds to be received sooner than had the original billing sequence been implemented, an optimized total amount of the funds to be received, an optimized number of payments to be received, an optimized schedule for the funds to be received, or some combination thereof.

At 1104, the processing device may receive, from another computing device of an insurance provider, a second request pertaining to the billing sequence. The second request may specify the insurance provider desires instant payment of their portion of the bills in the billing sequence, to be received sooner than had the original billing sequence been implemented, an optimized total amount of the funds to be received, an optimized number of payments to be received, an optimized schedule for the funds to be received, or some combination thereof.

At 1006, the processing device may modify, based on the first request and the second request, the billing sequence to generate a modified billing sequence, such that the modified billing sequence results in funds being received sooner than had the original billing sequence been implemented, an optimized total amount of the funds to be received, an optimized number of payments to be received, an optimized schedule for the funds to be received, or some combination thereof. The modified billing sequence may be generated to comply with the billing procedures. For example, the modified billing sequence may be generated to ensure that the modified billing sequence is free of medical billing fraud and/or balance billing.

Figure 12:
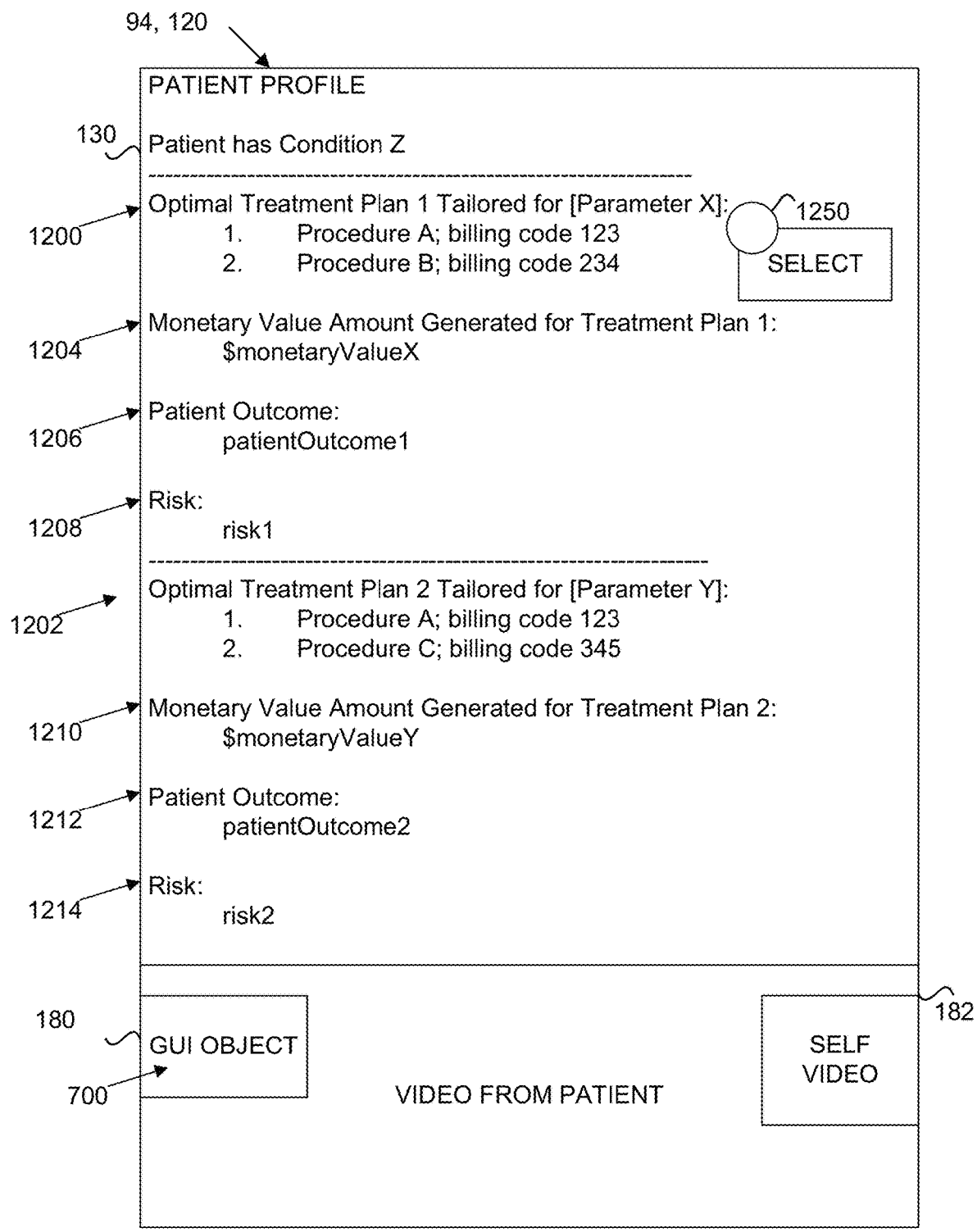
FIG. 12 shows an embodiment of the overview display of the assistant interface presenting, in real-time during a telemedicine session, optimal treatment plans that generate certain monetary value amounts and result in certain patient outcomes according to the present disclosure.

FIG. 12 shows an embodiment of the overview display 120 of the assistant interface 94 presenting, in real-time during a telemedicine session, optimal treatment plans that generate certain monetary value amounts and result in certain patient outcomes according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182. In some embodiments, the same optimal treatment plans, including monetary value amounts generated, patient outcomes, and/or risks, may be presented in a display screen 54 of the patient interface 50. In some embodiments, the optimal treatment plans including monetary value amounts generated, patient outcomes, and/or risks may be presented simultaneously, in real-time or near real-time, during a telehealth session, on both the display screen 54 of the patient interface 50 and the display screen 24 of the assistant interface 94.

The assistant (e.g., medical professional) using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the medical professional to share, in real-time or near real-time during the telemedicine session, the optimal treatment plans including the monetary value amounts generated, patient outcomes, risks, etc. with the patient on the patient interface 50. The medical professional may select the GUI object 700 to share the treatment plans. As depicted, another portion of the overview display 120 includes the patient profile display 130.

The patient profile display 130 is presenting two example optimal treatment plans 1200 and 1202. The optimal treatment plan 1200 includes a monetary value amount generated 1204 by the optimal treatment plan 1200, a patient outcome 1206 associated with performing the optimal treatment plan 1200, and a risk 1208 associated with performing the optimal treatment plan 1200. The optimal treatment plan 1202 includes a monetary value amount generated 1210 by the optimal treatment plan 1202, a patient outcome 1212 associated with performing the optimal treatment plan 1202, and a risk 1214 associated with performing the optimal treatment plan 1202. The risks may be determined using an algorithm that accounts for a difficulty of a procedure (e.g., open heart surgery versus an endoscopy), a skill level of a medical professional based on years of experience, malpractice judgments, and/or peer reviews, and various other factors.

To generate the optimal treatment plans 1200 and 1202, the artificial intelligence engine 11 may receive (i) information pertaining to a medical condition of the patient; (ii) a set of treatment plans that, when applied to patients having a similar medical condition as the patient, cause outcomes to be achieved by the patients; (ii) a set of monetary value amounts associated with the set of treatment plans; and/or (iii) a set of constraints including laws, regulations, and/or rules pertaining to billing codes associated with the set of treatment plans (e.g., more particularly, laws, regulations, and/or rules pertaining to billing codes associated with procedures and/or instructions included in the treatment plans).

Based on the set of treatment plans, the set of monetary value amounts, and the set of constraints, the artificial intelligence engine 11 may use one or more trained machine learning models 13 to generate the optimal treatment plans 1200 and 1202 for the patient. Each of the optimal treatment plans 1200 and 1202 complies with the set of constraints and represents a patient outcome and an associated monetary value amount generated. It should be noted that the optimal treatment plans may be generated and tailored based on one or more parameters (e.g., monetary value amount generated, patient outcome, and/or risk). The one or more parameters may be selected electronically by the artificial intelligence engine 11 or by a user (e.g., medical professional) using a user interface (e.g., patient profile display 130) to tailor how the treatment plans are optimized. For example, the user may specify she wants to see optimal treatment plans tailored based on the best patient outcome or, alternatively, based on the maximum monetary value amount generated.

Each of the respective treatment plans 1200 and 1202 may include one or more procedures to be performed on the patient based on the information pertaining to the medical condition of the patient. Further, each of the respective treatment plans 1200 and 1202 may include one or more billing codes associated with the one or more procedures.

For example, as depicted, the patient profile display 130 presents "Patient has Condition Z", where condition Z may be associated with information of the patient including a particular medical diagnosis code received from an EMR system. The patient profile display 130 also presents the optimal treatment plan 1200, "Optimal Treatment plan 1 Tailored for [Parameter X]: 1. Procedure A; billing code 123; 2. Procedure B; billing code 234". The [Parameter X] may be any suitable parameter, such as a monetary value amount generated by the optimal treatment plan, a patient outcome associated with performing the optimal treatment plan, and/or a risk associated with performing the optimal treatment plan.

The patient profile display 130 presents "Monetary Value Amount Generated for Treatment Plan 1: $monetaryValueX". monetaryValueX may be any suitable monetary value amount associated with the optimal treatment plan 1200. In some embodiments, monetaryValueX may be a configurable parameter that enables the user to set a desired monetary value amount to be generated.

The patient profile display 130 presents "Patient Outcome: patientOutcome1". patientOutcome1 may be any suitable patient outcome (e.g., full recovery or partial recovery, achievement of full or partial: desired range of motion, flexibility, strength, or pliability, etc.) associated with the optimal treatment plan 1200. In some embodiments, patientOutcome1 may be a configurable parameter that enables the user to set a desired patient outcome that results from performing the optimal treatment plan.

The patient profile display 130 presents "Risk: risk1". risk1 may be any suitable risk (e.g., low, medium, or high; or an absolute or relative number or magnitude on a scale; etc.) associated with the optimal treatment plan 1200. In some embodiments, risk1 may be a configurable parameter that enables the user to set a desired risk associated with performing the optimal treatment plan.

Further, the patient profile display 130 also presents the optimal treatment plan 1202, "Optimal Treatment plan 2 Tailored for [Parameter Y]: 1. Procedure A; billing code 123; 2. Procedure C; billing code 345". The [Parameter Y] may be any suitable parameter, such as a monetary value amount generated by the optimal treatment plan, a patient outcome associated with performing the optimal treatment plan, and/or a risk associated with performing the optimal treatment plan.

The patient profile display 130 presents "Monetary Value Amount Generated for Treatment Plan 1: $monetaryValueY". monetaryValueX may be any suitable monetary value amount associated with the optimal treatment plan 1202. In some embodiments, monetaryValueX may be a configurable parameter that enables the user to set a desired monetary value amount to be generated.

The patient profile display 130 presents "Patient Outcome: patientOutcome2". patientOutcome2 may be any suitable patient outcome (e.g., full recovery or partial recovery, achievement of full or partial: desired range of motion, flexibility, strength, or pliability, etc.) associated with the optimal treatment plan 1202. In some embodiments, patientOutcome2 may be a configurable parameter that enables the user to set a desired patient outcome that results from performing the optimal treatment plan.

The patient profile display 130 presents "Risk: risk2". Risk2 may be any suitable risk (e.g., low, medium, or high; or an absolute or relative number or magnitude on a scale; etc.) associated with the optimal treatment plan 1200. In some embodiments, risk2 may be a configurable parameter that enables the user to set a desired risk associated with performing the optimal treatment plan.

In the depicted example, the [Parameter X] and the [Parameter Y] both correspond to the parameter pertaining to the monetary value amount generated. The monetary value amount generated for [Parameter X] may be set higher than the monetary value amount generated for [Parameter Y]. Accordingly, the optimal treatment plan 1200 may include different procedures (e.g., Procedure A and Procedure B) that result in the higher monetary amount generated ([Parameter X]), a better outcome (e.g., patientOutcome1), and a higher risk (e.g., risk1) than the optimal treatment plan 1202, which may result in a lesser monetary value amount generated ([Parameter y]), less desirable outcome (e.g., patientOutcome2), and a lower risk (e.g., risk2).

Further, as depicted, a graphical element (e.g., button for "SELECT") may be presented in the patient profile display 130. Although just one graphical element is presented, any suitable number of graphical elements for selecting an optimal treatment may be presented in the patient profile display 130. As depicted, a user (e.g., medical professional or patient) uses an input peripheral (e.g., mouse, keyboard, microphone, touchscreen) to select (as represented by circle 1250) the graphical element associated with the optimal treatment plan 1200. The medical professional may prefer to receive a higher monetary value amount generated (e.g., [Parameter X]) from the optimal treatment plan and/or the patient may have requested the best patient outcome possible. Accordingly, the assistant interface 94 may transmit a control signal to the treatment apparatus 70 to control, based on the treatment plan 1200, operation of the treatment apparatus 70. In some embodiments, the patient may select the treatment plan from the display screen 54 and the patient interface 50 may transmit a control signal to the treatment apparatus 70 to control, based on the selected treatment plan 1200, operation of the treatment apparatus 70.

It should be noted that, in some embodiments, just treatment plans that pass muster with respect to standard of care, regulations, laws, and the like may be presented as viable options on a computing device of the patient and/or the medical professional. Accordingly, non-viable treatment plans that fail to meet a standard of care, violate a regulation and/or law, etc. may not be presented as options for selection. For example, the non-viable treatment plan options may be filtered from a result set presented on the computing device. In some embodiments, any treatment plan (e.g., both viable and non-viable options) may be presented on the computing device of the patient and/or medical professional.

Figure 13:
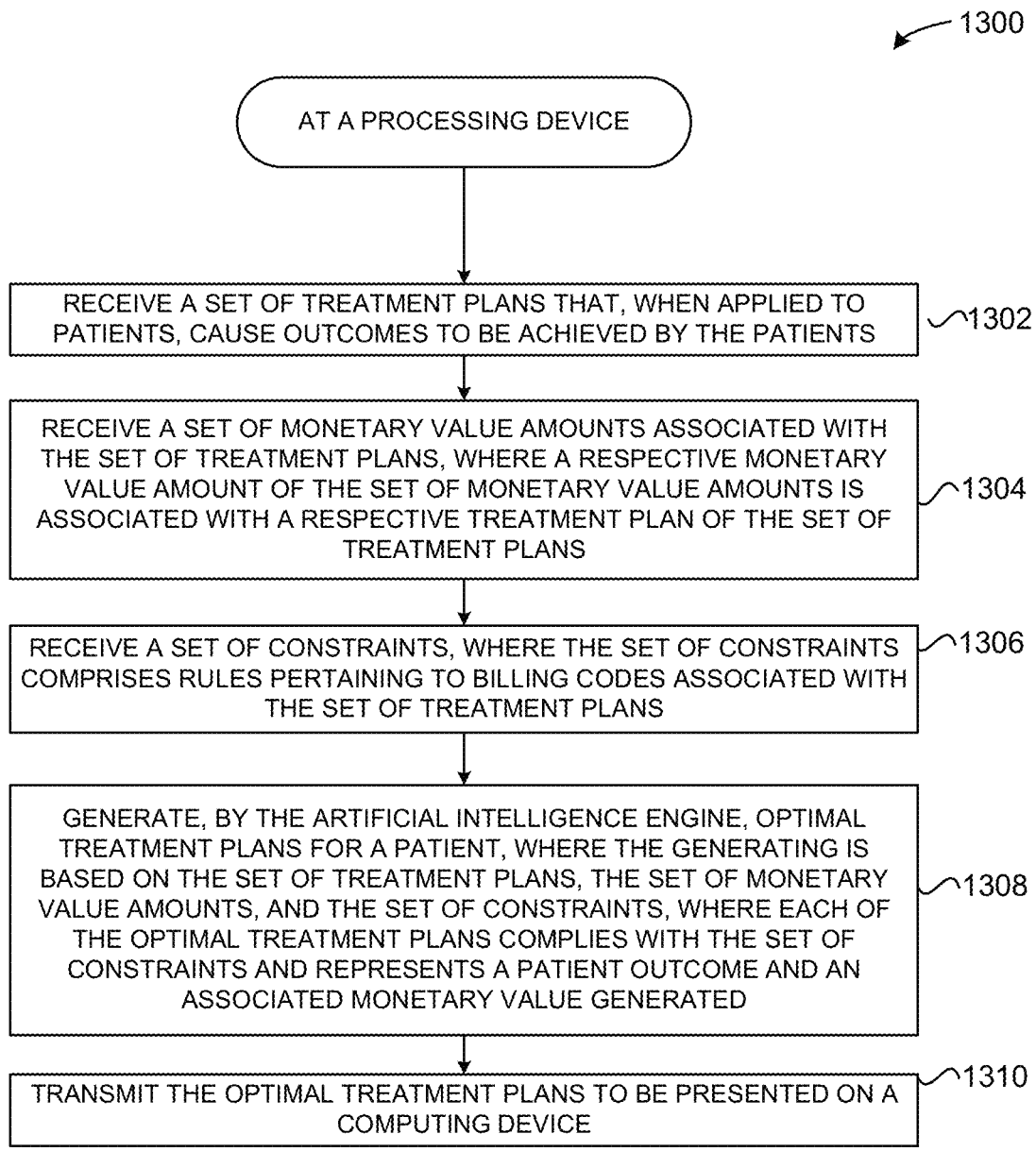
FIG. 13 shows an example embodiment of a method for generating optimal treatment plans for a patient, where the generating is based on a set of treatment plans, a set of money value amounts, and a set of constraints according to the present disclosure.

FIG. 13 shows an example embodiment of a method 1300 for generating optimal treatment plans for a patient, where the generating is based on a set of treatment plans, a set of monetary value amounts, and a set of constraints according to the present disclosure. Method 1300 includes operations performed by processors of a computing device (e.g., any component of FIG. 1, such as server 30 executing the artificial intelligence engine 11). In some embodiments, one or more operations of the method 1300 are implemented in computer instructions stored on a memory device and executed by a processing device. The method 1300 may be performed in the same or in a similar manner as described above in regard to method 1300. The operations of the method 1300 may be performed in some combination with any of the operations of any of the methods described herein.

Prior to the method 1300 beginning, the processing device may receive information pertaining to the patient. The information may include a medical diagnosis code and/or the various characteristics (e.g., personal information, performance information, and measurement information, etc.) described herein. The processing device may match the information of the patient with similar information from other patients. Based upon the matching, the processing device may select a set of treatment plans that cause certain outcomes (e.g., desired results) to be achieved by the patients.

At 1302, the processing device may receive the set of treatment plans that, when applied to patients, cause outcomes to be achieved by the patients. In some embodiments, the set of treatment plans may specify procedures to perform for the condition of the patient, a set of exercises to be performed by the patient using the treatment apparatus 70, a periodicity to perform the set of exercises using the treatment apparatus 70, a frequency to perform the set of exercises using the treatment apparatus 70, settings and/or configurations for portions (e.g., pedals, seat, etc.) of the treatment apparatus 70, and the like.

At 1304, the processing device may receive a set of monetary value amounts associated with the set of treatment plans. A respective monetary value amount of the set of monetary value amounts may be associated with a respective treatment plan of the set of treatment plans. For example, one respective monetary value amount may indicate $5,000 may be generated if the patient performs the respective treatment plan (e.g., including a consultation with a medical professional during a telemedicine session, rental fee for the treatment apparatus 70, follow-up in-person visit with the medical professional, etc.).

At 1306, the processing device may receive a set of constraints. The set of constraints may include rules pertaining to billing codes associated with the set of treatment plans. In some embodiments, the processing device may receive a set of billing codes associated with the procedures to be performed for the patient, the set of exercises, etc. and apply the set of billing codes to the treatment plans in view of the rules. In some embodiments, the set of constraints may further include constraints set forth in regulations, laws, or some combination thereof. For example, the laws and/or regulations may specify that certain billing codes (e.g., DRG or ICD-10) be used for certain procedures and/or exercises.

At 1308, the processing device may generate, by the artificial intelligence engine 11, optimal treatment plans for a patient. Generating the optimal treatment plans may be based on the set of treatment plans, the set of monetary value amounts, and the set of constraints. In some embodiments, generating the optimal treatment plans may include optimizing the optimal treatment plans for fees, revenue, profit (e.g., gross, net, etc.), earnings before interest (EBIT), earnings before interest, depreciation and amortization (EBITDA), cash flow, free cash flow, working capital, gross revenue, a value of warrants, options, equity, debt, derivatives or any other financial instrument, any generally acceptable financial measure or metric in corporate finance or according to Generally Accepted Accounting Principles (GAAP) or foreign counterparts, or some combination thereof.

Each of the optimal treatment plans complies with the set of constraints and represents a patient outcome and an associated monetary value amount generated. To ensure the procedure is allowed, the set of constraints may be enforced by comparing each procedure included in the optimal treatment plan with the set of constraints. If the procedure is allowed, based on the set of constraints, the procedure is included in the optimal treatment plan. If the procedure is not allowed, based on the set of constraints, the procedure is excluded from the optimal treatment plan. The optimal treatment plans may pertain to habilitation, prehabilitation, rehabilitation, post-habilitation, exercise, strength, pliability, flexibility, weight stability, weight gain, weight loss, cardiovascular fitness, performance or metrics, endurance, respiratory fitness, performance or metrics, or some combination thereof.

In some embodiments, a first optimal treatment plan of the optimal treatment plans may result in a first patient outcome and a first monetary value amount generated, and a second optimal treatment plan of the optimal treatment plans may result in a second patient outcome and a second monetary value amount generating. The second patient outcome may be better than the first patient outcome and the second monetary value amount generated may be greater than the first monetary value amount generated. Based on certain criteria (e.g., whether the patient desires the best patient outcome or has limited funds), either the first or second optimal treatment plan may be selected and implemented to control the treatment apparatus 70. In this and other scenarios herein, both patient outcomes, even the inferior one, are at or above the standard of care dictated by ethical medical practices for individual medical professionals, hospitals, etc., as the case may be, and such standard of care shall further be consistent with applicable governing regulations and laws, whether de facto or de jure.

At 1310, the processing device may transmit, in real-time or near real-time, the optimal treatment plans to be presented on a computing device of a medical professional. The optimal treatment plans may be presented on the computing device of the medical professional during a telemedicine or telehealth session in which a computing device of the patient is engaged. In some embodiments, the processing device may transmit the optimal treatment plans to be presented, in real-time or near real-time, on a computing device of the patient during a telemedicine session in which the computing device of the medical professional is engaged.

In some embodiments, the processing device may receive levels of risk associated with the set of treatment plans. In some embodiments, the levels of risk may be preconfigured for each of the set of treatment plans. In some embodiments, the levels of risk may be dynamically determined based on a number of factors (e.g., condition of the patient, difficulty of procedures included in the treatment plan, etc.). In some embodiments, generating the optimal treatment plans may also be based on the levels of risk. Further, in some embodiments, the processing device may transmit the optimal treatment plans and the levels of risk to be presented on the computing device of the medical professional. As used herein, "levels of risk" includes levels of risk for each of one or more risks.

Figure 14:
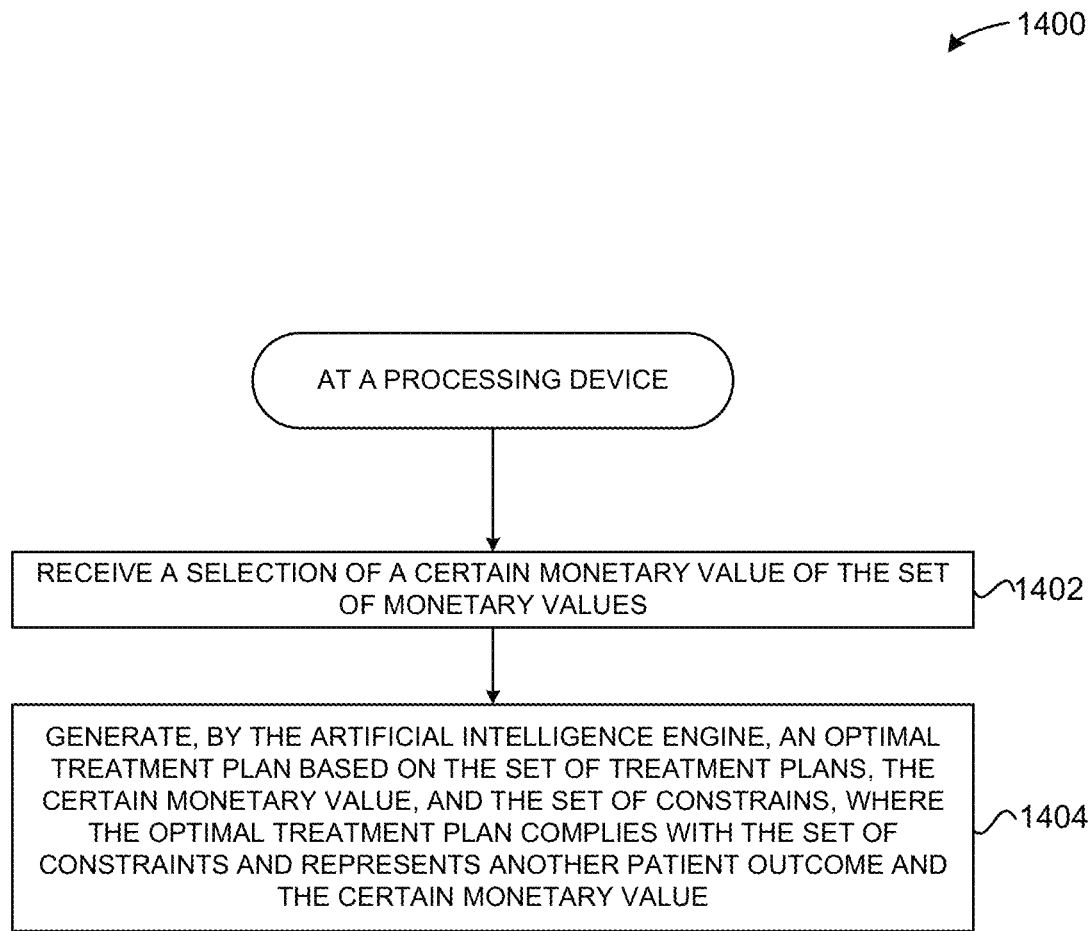
FIG. 14 shows an example embodiment of a method for receiving a selection of a monetary value amount and generating an optimal treatment plan based on a set of treatment plans, the monetary value amount, and a set of constraints according to the present disclosure.

FIG. 14 shows an example embodiment of a method 1400 for receiving a selection of a monetary value amount and generating an optimal treatment plan based on a set of treatment plans, the monetary value amount, and a set of constraints according to the present disclosure. Method 1400 includes operations performed by processors of a computing device (e.g., any component of FIG. 1, such as server 30 executing the artificial intelligence engine 11). In some embodiments, one or more operations of the method 1400 are implemented in computer instructions stored on a memory device and executed by a processing device. The method 1400 may be performed in the same or a similar manner as described above in regard to method 1000. The operations of the method 1400 may be performed in some combination with any of the operations of any of the methods described herein.

At 1402, the processing device may receive a selection of a certain monetary value amount of the set of monetary value amounts. For example, a graphical element included on a user interface of a computing device may enable a user to select (e.g., enter a monetary value amount in a textbox or select from a drop-down list, radio button, scrollbar, etc.) the certain monetary value amount to be generated by an optimal treatment plan. The certain monetary value amount may be transmitted to the artificial intelligence engine 11, which uses the certain monetary value amount to generate an optimal treatment plan tailored for the desired monetary value amount.

At 1404, the processing device may generate, by the artificial intelligence engine 11, an optimal treatment plan based on the set of treatment plans, the certain monetary value amount, and the set of constraints. The optimal treatment plan complies with the set of constraints and represents another patient outcome and the certain monetary value amount.

Figure 15:
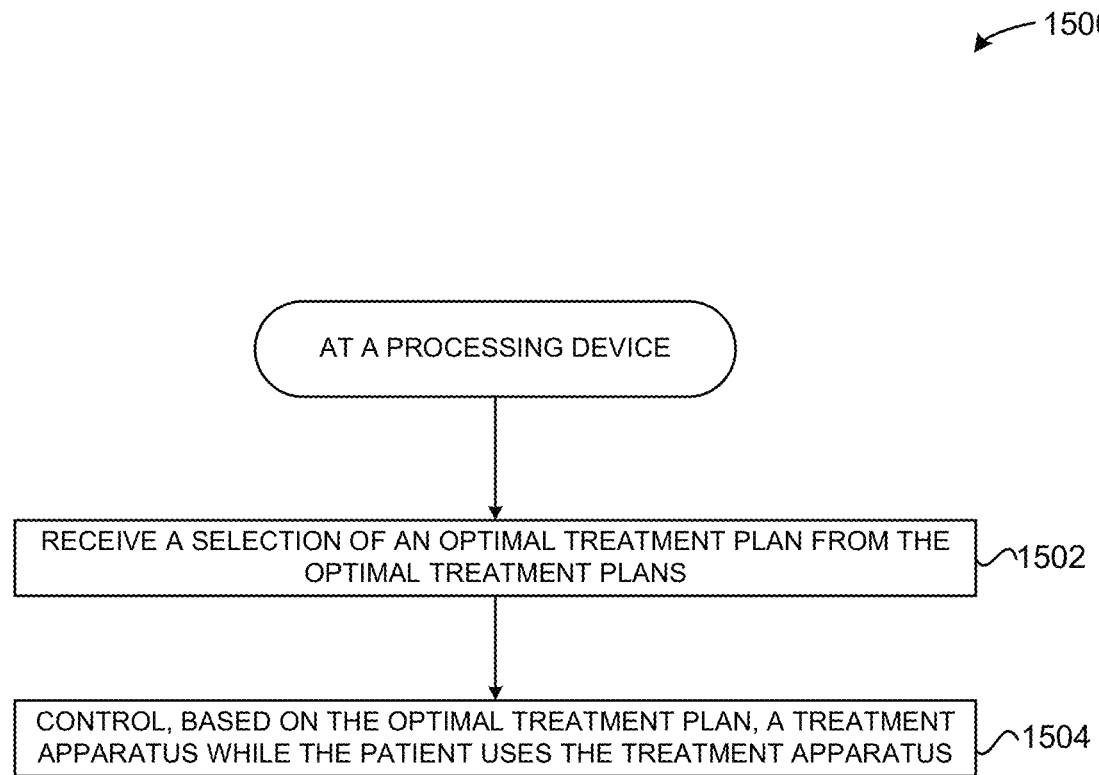
FIG. 15 shows an example embodiment of a method for receiving a selection of an optimal treatment plan and controlling, based on the optimal treatment plan, a treatment apparatus while the patient uses the treatment apparatus according to the present disclosure.

FIG. 15 shows an example embodiment of a method 1500 for receiving a selection of an optimal treatment plan and controlling, based on the optimal treatment plan, a treatment apparatus while the patient uses the treatment apparatus according to the present disclosure. Method 1500 includes operations performed by processors of a computing device (e.g., any component of FIG. 1, such as server 30 executing the artificial intelligence engine 11). In some embodiments, one or more operations of the method 1500 are implemented in computer instructions stored on a memory device and executed by a processing device. The method 1500 may be performed in the same or a similar manner as described above in regard to method 1000. The operations of the method 1500 may be performed in some combination with any of the operations of any of the methods described herein.

Prior to the method 1500 being executed, various optimal treatment plans may be generated by one or more trained machine learning models 13 of the artificial intelligence engine 11. For example, based on a set of treatment plans pertaining to a medical condition of a patient, a set of monetary value amounts associated with the set of treatment plans, and a set of constraints, the one or more trained machine learning models 13 may generate the optimal treatment plans. In some embodiments, the one or more trained machine learning models 13 may generate a billing sequence that is tailored based on a parameter (e.g., a fee to be paid to a medical professional, a payment plan for the patient to pay off an amount of money owed, a plan of reimbursement, a monetary value amount to be paid to an insurance provider, or some combination thereof). The various treatment plans and/or billing sequences may be transmitted to one or computing devices of a patient and/or medical professional.

At 1502 of the method 1500, the processing device may receive a selection of an optimal treatment plan from the optimal treatment plans. The selection may have been entered on a user interface presenting the optimal treatment plans on the patient interface 50 and/or the assistant interface 94. In some embodiments, the processing device may receive a selection of a billing sequence associated with at least a portion of a treatment plan. The selection may have been entered on a user interface presenting the billing sequence on the patient interface 50 and/or the assistant interface 94. If the user selects a particular billing sequence, the treatment plan associated with the selected billing sequence may be selected.

At 1504, the processing device may control, based on the selected optimal treatment plan, the treatment apparatus 70 while the patient uses the treatment apparatus. In some embodiments, the controlling is performed distally by the server 30. For example, if the selection is made using the patient interface 50, one or more control signals may be transmitted from the patient interface 50 to the treatment apparatus 70 to configure, according to the selected treatment plan, a setting of the treatment apparatus 70 to control operation of the treatment apparatus 70. Further, if the selection is made using the assistant interface 94, one or more control signals may be transmitted from the assistant interface 94 to the treatment apparatus 70 to configure, according to the selected treatment plan, a setting of the treatment apparatus 70 to control operation of the treatment apparatus 70.

It should be noted that, as the patient uses the treatment apparatus 70, the sensors 76 may transmit measurement data to a processing device. The processing device may dynamically control, according to the treatment plan, the treatment apparatus 70 by modifying, based on the sensor measurements, a setting of the treatment apparatus 70. For example, if the force measured by the sensor 76 indicates the user is not applying enough force to a pedal 102, the treatment plan may indicate to reduce the required amount of force for an exercise.

It should be noted that, as the patient uses the treatment apparatus 70, the user may use the patient interface 50 to enter input pertaining to a pain level experienced by the patient as the patient performs the treatment plan. For example, the user may enter a high degree of pain while pedaling with the pedals 102 set to a certain range of motion on the treatment apparatus 70. The pain level may cause the range of motion to be dynamically adjusted based on the treatment plan. For example, the treatment plan may specify alternative range of motion settings if a certain pain level is indicated when the user is performing an exercise at a certain range of motion.

Different people have different tolerances for pain. In some embodiments, a person may indicate a pain level they are willing to tolerate to achieve a certain result (e.g., a certain range of motion within a certain time period). A high degree of pain may be acceptable to a person if that degree of pain is associated with achieving the certain result. The treatment plan may be tailored based on the indicated pain level. For example, the treatment plan may include certain exercises, frequencies of exercises, and/or periodicities of exercises that are associated with the indicated pain level and desired result for people having characteristics similar to characteristics of the person.

Figure 16:
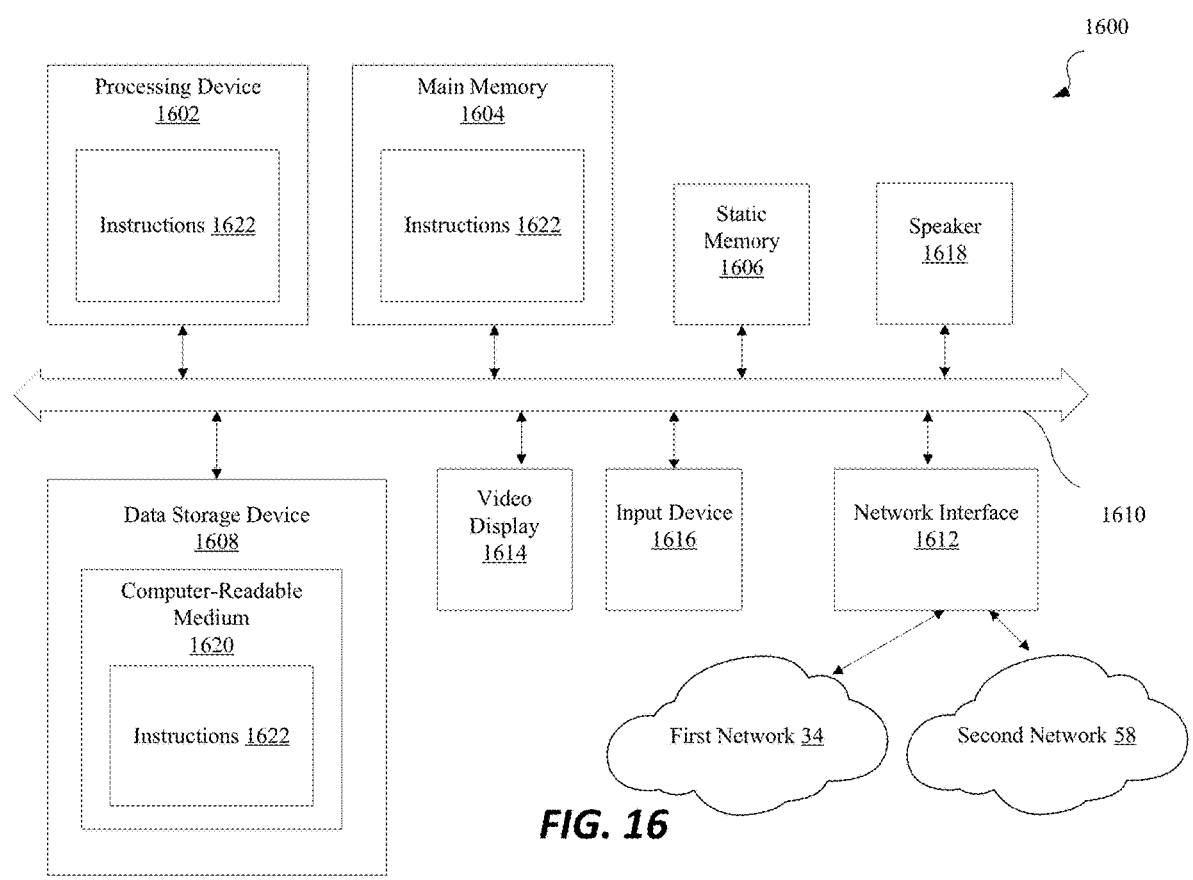
FIG. 16 shows an example computer system according to the present disclosure.

FIG. 16 shows an example computer system 1600 which can perform any one or more of the methods described herein, in accordance with one or more aspects of the present disclosure. In one example, computer system 1600 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1600 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1600 includes a processing device 1602, a main memory 1604 (e.g., read-only memory (ROM), flash memory, solid state drives (SSDs), dynamic random access memory (DRAM) such as synchronous DRAM (SDRAM)), a static memory 1606 (e.g., flash memory, solid state drives (SSDs), static random access memory (SRAM)), and a data storage device 1608, which communicate with each other via a bus 1610.

Processing device 1602 represents one or more general-purpose processing devices such as a microprocessor, central processing unit, or the like. More particularly, the processing device 1602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1600 may further include a network interface device 1612. The computer system 1600 also may include a video display 1614 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1616 (e.g., a keyboard and/or a mouse or a gaming-like control), and one or more speakers 1618 (e.g., a speaker). In one illustrative example, the video display 1614 and the input device(s) 1616 may be combined into a single component or device (e.g., an LCD touch screen).

The data storage device 1616 may include a computer-readable medium 1620 on which the instructions 1622 embodying any one or more of the methods, operations, or functions described herein is stored. The instructions 1622 may also reside, completely or at least partially, within the main memory 1604 and/or within the processing device 1602 during execution thereof by the computer system 1600. As such, the main memory 1604 and the processing device 1602 also constitute computer-readable media. The instructions 1622 may further be transmitted or received over a network via the network interface device 1612.

While the computer-readable storage medium 1620 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A method for generating, by an artificial intelligence engine, a treatment plan and a billing sequence associated with the treatment plan, the method comprising:

receiving information pertaining to a patient, wherein the information comprises a medical diagnosis code of the patient;

generating, based on the information, the treatment plan for the patient, wherein the treatment plan comprises a plurality of instructions for the patient to follow;

receiving a set of billing procedures associated with the plurality of instructions, wherein the set of billing procedures comprises rules pertaining to billing codes, timing, constraints, or some combination thereof;

generating, based on the set of billing procedures, the billing sequence for at least a portion of the plurality of instructions, wherein the billing sequence is tailored according to a certain parameter; and transmitting the treatment plan and the billing sequence to a computing device.

Clause 2. The method of any preceding clause, further comprising distally controlling, based on the treatment plan, a treatment apparatus used by the patient to perform the treatment plan.

Clause 3. The method of any preceding clause, wherein the certain parameter is a fee to be paid to a medical professional, a payment plan for the patient to pay off an amount of money owed, a plan of reimbursement, an amount of revenue to be paid to an insurance provider, or some combination thereof.

Clause 4. The method of any preceding clause, wherein the treatment plan is for habilitation, pre-habilitation, rehabilitation, post-habilitation, exercise, strength training, endurance training, weight loss, weight gain, flexibility, pliability, or some combination thereof.

Clause 5. The method of any preceding clause, wherein the plurality of instructions comprises:

a plurality of exercises for the patient to perform,
an order for the plurality of exercises,
a frequency for performing the plurality of exercises,
a diet regimen,
a sleep regimen,
a plurality of procedures to perform on the patient,
an order for the plurality of procedures,
a medication regimen,
a plurality of sessions for the patient, or
some combination thereof.

Clause 6. The method of any preceding clause, further comprising causing presentation, in real-time or near real-time during a telemedicine session with another computing device of the patient, of the treatment plan and the billing sequence on the computing device of a medical professional.

Clause 7. The method of any preceding clause, further comprising:

receiving, from the computing device, a first request pertaining to the billing sequence;

receiving, from another computing device of an insurance provider, a second request pertaining to the billing sequence;

modifying, based on the first request and the second request, the billing sequence to generate a modified billing sequence, such that the modified billing sequence results in funds being received sooner than had the billing sequence been implemented, an optimized total amount of the funds being received, an optimized number of payments being received, an optimized schedule for the funds being received, or some combination thereof.

Clause 8. The method of any preceding clause, wherein the constraints further comprise constraints set forth in regulations, laws, or some combination thereof.

Clause 9. The method of any preceding clause, further comprising transmitting the treatment plan and the billing sequence to be presented on a second computing device of the patient in real-time or near real-time during a telemedicine session in which the computing device of the medical professional is engaged.

Clause 10. A system, comprising:

a memory device storing instructions;

a processing device communicatively coupled to the memory device, the processing device executes the instructions to:

receive information pertaining to a patient, wherein the information comprises a medical diagnosis code of the patient;

generate, based on the information, a treatment plan for the patient, wherein the treatment plan comprises a plurality of instructions for the patient to follow;

receive a set of billing procedures associated with the plurality of instructions, wherein the set of billing procedures comprises rules pertaining to billing codes, timing, constraints, or some combination thereof;

generate, based on the set of billing procedures, a billing sequence for at least a portion of the plurality of instructions, wherein the billing sequence is tailored according to a certain parameter; and transmit the treatment plan and the billing sequence to a computing device.

Clause 11. The system of any preceding clause, wherein the processing device is further to distally control, based on the treatment plan, a treatment apparatus used by the patient to perform the treatment plan.

Clause 12. The system of any preceding clause, wherein the certain parameter is a fee to be paid to a medical professional, a payment plan for the patient to pay off an amount of money owed, a plan of reimbursement, an amount of revenue to be paid to an insurance provider, or some combination thereof.

Clause 13. The system of any preceding clause, wherein the treatment plan is for habilitation, pre-habilitation, rehabilitation, post-habilitation, exercise, strength training, endurance training, weight loss, weight gain, flexibility, pliability, or some combination thereof.

Clause 14. The system of any preceding clause, wherein the plurality of instructions comprises:

a plurality of exercises for the patient to perform,
an order for the plurality of exercises,
a frequency for performing the plurality of exercises,
a diet regimen,
a sleep regimen,
a plurality of procedures to perform on the patient,
an order for the plurality of procedures,
a medication regimen,
a plurality of sessions for the patient, or
some combination thereof.

Clause 15. The system of any preceding clause, wherein the processing device is further to cause presentation, in real-time or near real-time during a telemedicine session with another computing device of the patient, of the treatment plan and the billing sequence on the computing device of a medical professional.

Clause 16. The system of any preceding clause, wherein the processing device is further to:

receive, from the computing device, a first request pertaining to the billing sequence;

receive, from another computing device of an insurance provider, a second request pertaining to the billing sequence;

modify, based on the first request and the second request, the billing sequence to generate a modified billing sequence, such that the modified billing sequence results in funds being received sooner than had the billing sequence been implemented, an optimized total amount of the funds being received, an optimized number of payments being received, an optimized schedule for the funds being received, or some combination thereof.

Clause 17. The system of any preceding clause, wherein the constraints further comprise constraints set forth in regulations, laws, or some combination thereof.

Clause 18. The system of any preceding clause, wherein the processing device is further to transmit the treatment plan and the billing sequence to be presented on a second computing device of the patient in real-time or near real-time during a telemedicine session in which the computing device of the medical professional is engaged.

Clause 19. A tangible, non-transitory computer-readable medium storing instructions that, when executed, cause a processing device to:

receive information pertaining to a patient, wherein the information comprises a medical diagnosis code of the patient;

generate, based on the information, a treatment plan for the patient, wherein the treatment plan comprises a plurality of instructions for the patient to follow;

receive a set of billing procedures associated with the plurality of instructions, wherein the set of billing procedures comprises rules pertaining to billing codes, timing, constraints, or some combination thereof;

generate, based on the set of billing procedures, a billing sequence for at least a portion of the plurality of instructions, wherein the billing sequence is tailored according to a certain parameter; and transmit the treatment plan and the billing sequence to a computing device.

Clause 20. The computer-readable medium of any preceding clause, wherein the processing device is further to distally control, based on the treatment plan, a treatment apparatus used by the patient to perform the treatment plan.

Clause 21. A method for generating, by an artificial intelligence engine, treatment plans for optimizing patient outcome and monetary value amount generated, the method comprising:

receiving a set of treatment plans that, when applied to patients, cause outcomes to be achieved by the patients;

receiving a set of monetary value amounts associated with the set of treatment plans, wherein a respective monetary value amount of the set of monetary value amounts is associated with a respective treatment plan of the set of treatment plans;

receiving a set of constraints, wherein the set of constraints comprises rules pertaining to billing codes associated with the set of treatment plans;

generating, by the artificial intelligence engine, optimal treatment plans for a patient, wherein the generating is based on the set of treatment plans, the set of monetary value amounts, and the set of constraints, wherein each of the optimal treatment plans complies with the set of constraints and represents a patient outcome and an associated monetary value amount generated; and transmitting the optimal treatment plans to be presented on a computing device.

Clause 22. The method of any preceding clause, wherein the optimal treatment plans are for habilitation, pre-habilitation, rehabilitation, post-habilitation, exercise, strength, pliability, flexibility, weight stability, weight gain, weight loss, cardiovascular, endurance, respiratory, or some combination thereof.

Clause 23. The method of any preceding clause, further comprising:

receiving a selection of a certain monetary value amount of the set of monetary value amounts; and generating, by the artificial intelligence engine, an optimal treatment plan based on the set of treatment plans, the certain monetary value amount, and the set of constraints, wherein the optimal treatment plan complies with the set of constraints and represents another patient outcome and the certain monetary value amount.

Clause 24. The method of any preceding clause, wherein the set of treatment plans specifies a set of exercises to be performed by the patient using a treatment apparatus, and the method further comprises:

receiving a set of billing codes associated with the set of exercises; and correlating the set of billing codes with the rules.

Clause 25. The method of any preceding clause, further comprising:

receiving levels of risk associated with the set of treatment plans, wherein the generating the optimal treatment plans is also based on the levels of risk; and transmitting the optimal treatment plans and the level of risks to be presented on the computing device of the medical professional.

Clause 26. The method of any preceding clause, wherein:

a first optimal treatment plan of the optimal treatment plans results in a first patient outcome and a first monetary value amount generated; and a second optimal treatment plan of the optimal treatment plans results in a second patient outcome and a second monetary value amount generated, wherein the second patient outcome is better than the first patient outcome and the second revenue value generated is greater than the first monetary value amount generated.

Clause 27. The method of any preceding clause, wherein the set of constraints further comprises constraints set forth in regulations, laws, or some combination thereof.

Clause 28. The method of any preceding clause, further comprising transmitting the optimal treatment plans to be presented on a computing device of the patient in real-time or near real-time during a telemedicine session in which the computing device of the medical professional is engaged.

Clause 29. The method of any preceding clause, further comprising:

receiving a selection of an optimal treatment plan from the optimal treatment plans; and controlling, based on the optimal treatment plan, a treatment apparatus while the patient uses the treatment apparatus.

Clause 30. The method of any preceding clause, wherein the controlling is performed distally.

Clause 31. The method of any preceding clause, wherein:
the optimal treatment plans are presented on the computing device of a medical professional during a telemedicine session in which a computing device of the patient is engaged.

Clause 32. The method of any preceding clause, wherein:
the optimal treatment plans are presented on the computing device of patient during a telemedicine session in which a computing device of a medical professional is engaged.

Clause 33. The method of any preceding clause, wherein the generating, based on the set of treatment plans, the set of monetary value amounts, and the set of constraints, the optimal treatment plans further comprises optimizing the optimal treatment plans for revenue generated, profit generated, cash flow generated, free cash flow generated, gross revenue generated, earnings before interest taxes amortization (EBITA) generated, or some combination thereof.

Clause 34. A system, comprising:
a memory device storing instructions; and
a processing device communicatively coupled to the memory device, the processing device executes the instructions to:
receive a set of treatment plans that, when applied to patients, cause outcomes to be achieved by the patients;
receive a set of monetary value amounts associated with the set of treatment plans, wherein a respective monetary value amount of the set of monetary value amounts is associated with a respective treatment plan of the set of treatment plans;
receive a set of constraints, wherein the set of constraints comprises rules pertaining to billing codes associated with the set of treatment plans;
generate, by an artificial intelligence engine, optimal treatment plans for a patient, wherein the generating is based on the set of treatment plans, the set of monetary value amounts, and the set of constraints, wherein each of the optimal treatment plans complies with the set of constraints and represents a patient outcome and an associated monetary value amount generated; and
transmit the optimal treatment plans to be presented on a computing device.

Clause 35. The system of any preceding clause, wherein the optimal treatment plans are for habilitation, pre-habilitation, rehabilitation, post-habilitation, exercise, strength, pliability, flexibility, weight stability, weight gain, weight loss, cardiovascular, endurance, respiratory, or some combination thereof.

Clause 36. The system of any preceding clause, wherein the processing device is further to:
receive a selection of a certain monetary value amount of the set of monetary value amounts; and
generate, by the artificial intelligence engine, an optimal treatment plan based on the set of treatment plans, the certain monetary value amount, and the set of constraints, wherein the optimal treatment plan complies with the set of constraints and represents another patient outcome and the certain monetary value amount.

Clause 37. The system of any preceding clause, wherein the set of treatment plans specifies a set of exercises to be performed by the patient using a treatment apparatus, and the processing device is further to:
receive a set of billing codes associated with the set of exercises; and
correlate the set of billing codes with the rules.

Clause 38. The system of any preceding clause, wherein the processing device is further to:
receive levels of risk associated with the set of treatment plans, wherein the generating the optimal treatment plans is also based on the levels of risk; and
transmit the optimal treatment plans and the level of risks to be presented on the computing device of the medical professional.

Clause 39. The system of any preceding clause, wherein:
a first optimal treatment plan of the optimal treatment plans results in a first patient outcome and a first monetary value amount generated; and
a second optimal treatment plan of the optimal treatment plans results in a second patient outcome and a second monetary value amount generated, wherein the second patient outcome is better than the first patient outcome and the second revenue value generated is greater than the first monetary value amount generated.

Clause 40. A tangible, non-transitory computer-readable medium storing instructions that, when executed, cause a processing device to:
receive a set of treatment plans that, when applied to patients, cause outcomes to be achieved by the patients;
receive a set of monetary value amounts associated with the set of treatment plans, wherein a respective monetary value amount of the set of monetary value amounts is associated with a respective treatment plan of the set of treatment plans;
receive a set of constraints, wherein the set of constraints comprises rules pertaining to billing codes associated with the set of treatment plans;
generate, by an artificial intelligence engine, optimal treatment plans for a patient, wherein the generating is based on the set of treatment plans, the set of monetary value amounts, and the set of constraints, wherein each of the optimal treatment plans complies with the set of constraints and represents a patient outcome and an associated monetary value amount generated; and
transmit the optimal treatment plans to be presented on a computing device.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:
1. A method comprising:
receiving, by a device, information pertaining to a patient, the information comprising a medical diagnosis code of the patient;
generating, via execution of an artificial intelligence (AI) engine by the device, based on the received information, a treatment plan for the patient, the treatment plan comprising a plurality of instructions for the patient to follow;

receiving, by the device, a set of billing procedures associated with the plurality of instructions, the set of billing procedures comprising rules pertaining to billing codes, timing, constraints, or some combination thereof;

generating, via execution of the AI engine by the device, based on the set of billing procedures, the billing sequence for at least a portion of the plurality of instructions, the billing sequence being tailored according to a certain parameter;

transmitting over a network, by the device, the treatment plan and the billing sequence to a computing device associated with the patient;

establishing, over the network, by the device, a telehealth session with the patient; and based at least on the transmitted treatment plan, distally controlling, by the device over the network, during the established telehealth session, the computing device, such that the distal control causes the computing device to perform operations, via the distal control of the device, in accordance with the treatment plan.

2. The method of claim 1, wherein the computing device is associated with a treatment apparatus or constitutes the treatment apparatus.

3. The method of claim 1, wherein the certain parameter is a fee to be paid to a medical professional, a payment plan for the patient to pay off an amount of money owed, a plan of reimbursement, an amount of revenue to be paid to an insurance provider, or some combination thereof.

4. The method of claim 1, wherein the treatment plan is for habilitation, pre-habilitation, rehabilitation, post-habilitation, exercise, strength training, endurance training, weight loss, weight gain, flexibility, pliability, or some combination thereof.

5. The method of claim 1, wherein the plurality of instructions comprises:
a plurality of exercises for the patient to perform,
an order for the plurality of exercises,
a frequency for performing the plurality of exercises,
a diet regimen,
a sleep regimen,
a plurality of procedures to perform on the patient,
an order for the plurality of procedures,
a medication regimen,
a plurality of sessions for the patient, or
some combination thereof.

6. The method of claim 1, further comprising causing presentation, in real-time or near real-time during a telemedicine session with another computing device of the patient, of the treatment plan and the billing sequence on a computing device of a medical professional.

7. The method of claim 1, further comprising:
receiving, from the computing device, a first request pertaining to the billing sequence;
receiving, from another computing device of an insurance provider, a second request pertaining to the billing sequence; and
modifying, based on the first request and the second request, the billing sequence to generate a modified billing sequence, such that the modified billing sequence results in funds being received sooner than had the billing sequence been implemented, an optimized total amount of the funds being received, an optimized number of payments being received, an optimized schedule for the funds being received, or some combination thereof.

8. The method of claim 1, wherein the constraints further comprise constraints set forth in regulations, laws, or some combination thereof.

9. The method of claim 1, further comprising transmitting the treatment plan and the billing sequence to be presented on a second computing device of the patient in real-time or near real-time during a telemedicine session in which a computing device of the medical professional is engaged.

10. A system comprising:
a memory device storing instructions;
a processing device communicatively coupled to the memory device, the processing device executes the instructions to:
receive information pertaining to a patient, the information comprising a medical diagnosis code of the patient;
generate, via execution of an artificial intelligence (AI) engine, based on the received information, a treatment plan for the patient, the treatment plan comprising a plurality of instructions for the patient to follow;
receive a set of billing procedures associated with the plurality of instructions, the set of billing procedures comprising rules pertaining to billing codes, timing, constraints, or some combination thereof;
generate, via execution of the AI engine, based on the set of billing procedures, the billing sequence for at least a portion of the plurality of instructions, the billing sequence being tailored according to a certain parameter;
transmit, over a network, the treatment plan and the billing sequence to a computing device associated with the patient;
establish, over the network, a telehealth session with the patient; and
based at least on the transmitted treatment plan, distally control, over the network, during the established telehealth session, the computing device, such that the distal control causes the computing device to perform operations, via the distal control of the device, in accordance with the treatment plan.

11. The system of claim 10, wherein the computing device is associated with a treatment apparatus or constitutes the treatment apparatus.

12. The system of claim 10, wherein the certain parameter is a fee to be paid to a medical professional, a payment plan for the patient to pay off an amount of money owed, a plan of reimbursement, an amount of revenue to be paid to an insurance provider, or some combination thereof.

13. The system of claim 10, wherein the treatment plan is for habilitation, pre-habilitation, rehabilitation, post-habilitation, exercise, strength training, endurance training, weight loss, weight gain, flexibility, pliability, or some combination thereof.

14. The system of claim 10, wherein the plurality of instructions comprises:
a plurality of exercises for the patient to perform,
an order for the plurality of exercises,
a frequency for performing the plurality of exercises,
a diet regimen,
a sleep regimen,
a plurality of procedures to perform on the patient,
an order for the plurality of procedures,
a medication regimen,
a plurality of sessions for the patient, or
some combination thereof.

15. The system of claim 10, wherein the processing device is further to cause presentation, in real-time or near real-time during a telemedicine session with another computing device of the patient, of the treatment plan and the billing sequence on a computing device of a medical professional.

16. The system of claim 10, wherein the processing device is further to:
receive, from the computing device, a first request pertaining to the billing sequence;
receive, from another computing device of an insurance provider, a second request pertaining to the billing sequence; and
modify, based on the first request and the second request, the billing sequence to generate a modified billing sequence, such that the modified billing sequence results in funds being received sooner than had the billing sequence been implemented, an optimized total amount of the funds being received, an optimized number of payments being received, an optimized schedule for the funds being received, or some combination thereof.

17. The system of claim 10, wherein the constraints further comprise constraints set forth in regulations, laws, or some combination thereof.

18. The system of claim 10, wherein the processing device is further to transmit the treatment plan and the billing sequence to be presented on a second computing device of the patient in real-time or near real-time during a telemedicine session in which a computing device of the medical professional is engaged.

19. A non-transitory computer-readable storage medium tangibly encoded with computer-executable instructions, that when executed by a processing device, cause the processing device to:
receive information pertaining to a patient, the information comprising a medical diagnosis code of the patient;
generate, via execution of an artificial intelligence (AI) engine, based on the received information, a treatment plan for the patient, the treatment plan comprising a plurality of instructions for the patient to follow;
receive a set of billing procedures associated with the plurality of instructions, the set of billing procedures comprising rules pertaining to billing codes, timing, constraints, or some combination thereof;
generate, via execution of the AI engine, based on the set of billing procedures, the billing sequence for at least a portion of the plurality of instructions, the billing sequence being tailored according to a certain parameter;
transmit, over a network, the treatment plan and the billing sequence to a computing device associated with the patient;
establish, over the network, a telehealth session with the patient; and
based at least on the transmitted treatment plan, distally control, over the network, during the established telehealth session, the computing device, such that the distal control causes the computing device to perform operations, via the distal control of the device, in accordance with the treatment plan.

20. The non-transitory computer-readable storage medium of claim 19, wherein the computing device is associated with a treatment apparatus or constitutes the treatment apparatus.

* * * * *